(12) United States Patent
Buzby

(10) Patent No.: US 7,482,120 B2
(45) Date of Patent: *Jan. 27, 2009

(54) METHODS AND COMPOSITIONS FOR IMPROVING FIDELITY IN A NUCLEIC ACID SYNTHESIS REACTION

(75) Inventor: Philip Richard Buzby, Brockton, MA (US)

(73) Assignee: Helicos Biosciences Corporation, Cambridge, MA (US)

( * ) Notice: Subject to any disclaimer, the term of this patent is extended or adjusted under 35 U.S.C. 154(b) by 200 days.

This patent is subject to a terminal disclaimer.

(21) Appl. No.: 11/046,448

(22) Filed: Jan. 28, 2005

(65) Prior Publication Data

US 2006/0172313 A1    Aug. 3, 2006

(51) Int. Cl.
*C12P 19/34* (2006.01)
*C12Q 1/68* (2006.01)

(52) U.S. Cl. .......................................... 435/6; 435/91.2

(58) Field of Classification Search ....................... None
See application file for complete search history.

(56) References Cited

U.S. PATENT DOCUMENTS

| | | |
|---|---|---|
| 3,996,345 A | 12/1976 | Ullman et al. |
| 4,119,368 A | 10/1978 | Yamazaki |
| 4,153,855 A | 5/1979 | Feingold |
| 4,344,064 A | 8/1982 | Bitler et al. |
| 4,351,760 A | 9/1982 | Khanna et al. |
| 4,683,195 A | 7/1987 | Mullis et al. |
| 4,683,202 A | 7/1987 | Mullis |
| 4,707,237 A | 11/1987 | Lepp et al. |
| 4,711,955 A | 12/1987 | Ward et al. |
| 4,725,677 A | 2/1988 | Koster et al. |
| 4,739,044 A | 4/1988 | Stabinsky |
| 4,757,141 A | 7/1988 | Fung et al. |
| 4,793,705 A | 12/1988 | Shera |
| 4,811,218 A | 3/1989 | Hunkapiller et al. |
| 4,863,849 A | 9/1989 | Melamede |
| 4,865,968 A | 9/1989 | Orgel et al. |
| 4,889,818 A | 12/1989 | Gelfand et al. |
| 4,942,124 A | 7/1990 | Church |
| 4,962,037 A | 10/1990 | Jett et al. |

(Continued)

FOREIGN PATENT DOCUMENTS

DE    10256898 A1    9/2004

(Continued)

OTHER PUBLICATIONS

International Search Report dated Jul. 25, 2006.

(Continued)

*Primary Examiner*—Gary Benzion
*Assistant Examiner*—Stephanie K Mummert
(74) *Attorney, Agent, or Firm*—Cooley Godward Kronish LLP; Konstantin M. Linnik; Thomas C. Meyers (57) ABSTRACT

The invention provides methods and compositions for improving the fidelity of a sequencing-by-synthesis reaction by using a nucleotide derivative that forms a hydrogen bond with a complementary nucleotide on a template, but fails to form a phosphodiester bond with the 3' hydroxyl group of a primer under conditions otherwise suitable for a polymerization reaction; thereby blocking incorporation of a mismatched nucleotide.

30 Claims, 2 Drawing Sheets

U.S. PATENT DOCUMENTS

| | | |
|---|---|---|
| 4,971,903 A | 11/1990 | Hyman |
| 4,979,824 A | 12/1990 | Mathies et al. |
| 4,994,368 A | 2/1991 | Goodman et al. |
| 4,994,372 A | 2/1991 | Tabor et al. |
| 4,994,373 A | 2/1991 | Stavrianopoulos et al. |
| 5,085,562 A | 2/1992 | van Lintel |
| 5,091,652 A | 2/1992 | Mathies et al. |
| 5,096,388 A | 3/1992 | Weinberg |
| 5,096,554 A | 3/1992 | Chin et al. |
| 5,108,892 A | 4/1992 | Burke et al. |
| 5,112,736 A | 5/1992 | Caldwell et al. |
| RE34,069 E | 9/1992 | Koster et al. |
| 5,143,854 A | 9/1992 | Pirrung et al. |
| 5,167,784 A | 12/1992 | Noolandi |
| 5,171,132 A | 12/1992 | Miyazaki et al. |
| 5,198,540 A | 3/1993 | Koster |
| 5,209,834 A | 5/1993 | Shera |
| 5,224,843 A | 7/1993 | van Lintel |
| 5,242,796 A | 9/1993 | Prober et al. |
| 5,242,797 A | 9/1993 | Hirschfeld |
| 5,258,506 A | 11/1993 | Urdea et al. |
| 5,259,737 A | 11/1993 | Kamisuki et al. |
| 5,260,433 A | 11/1993 | Engelhardt et al. |
| 5,265,327 A | 11/1993 | Faris et al. |
| 5,267,152 A | 11/1993 | Yang et al. |
| 5,302,509 A | 4/1994 | Cheeseman |
| 5,304,487 A | 4/1994 | Wilding et al. |
| 5,306,403 A | 4/1994 | Vo-Dinh |
| 5,336,062 A | 8/1994 | Richter |
| 5,360,523 A | 11/1994 | Middendorf et al. |
| 5,375,979 A | 12/1994 | Trah |
| 5,376,252 A | 12/1994 | Ekstrom et al. |
| 5,403,709 A | 4/1995 | Agrawal et al. |
| 5,405,747 A | 4/1995 | Jett et al. |
| 5,405,783 A | 4/1995 | Pirrung et al. |
| 5,409,811 A | 4/1995 | Tabor et al. |
| 5,424,186 A | 6/1995 | Fodor et al. |
| 5,436,149 A | 7/1995 | Barnes |
| 5,449,767 A | 9/1995 | Ward et al. |
| 5,476,928 A | 12/1995 | Ward et al. |
| 5,484,701 A | 1/1996 | Cocuzza et al. |
| 5,492,806 A | 2/1996 | Drmanac et al. |
| 5,514,256 A | 5/1996 | Douthart et al. |
| 5,518,900 A | 5/1996 | Nikiforov et al. |
| 5,525,464 A | 6/1996 | Drmanac et al. |
| 5,529,465 A | 6/1996 | Zengerle et al. |
| 5,534,125 A | 7/1996 | Middendorf et al. |
| 5,547,839 A | 8/1996 | Dower et al. |
| 5,547,859 A | 8/1996 | Goodman et al. |
| 5,556,790 A | 9/1996 | Pettit |
| 5,558,991 A | 9/1996 | Trainor |
| 5,599,695 A | 2/1997 | Pease et al. |
| 5,610,287 A | 3/1997 | Nikiforov et al. |
| 5,631,734 A | 5/1997 | Stern et al. |
| 5,632,957 A | 5/1997 | Heller et al. |
| 5,654,149 A | 8/1997 | Mendoza et al. |
| 5,659,171 A | 8/1997 | Young et al. |
| 5,670,346 A | 9/1997 | Reeve et al. |
| 5,674,716 A | 10/1997 | Tabor et al. |
| 5,675,155 A | 10/1997 | Pentoney, Jr. et al. |
| 5,688,648 A | 11/1997 | Mathies et al. |
| 5,695,940 A | 12/1997 | Drmanac et al. |
| 5,705,018 A | 1/1998 | Hartley |
| 5,707,506 A | 1/1998 | Douthart et al. |
| 5,710,628 A | 1/1998 | Waterhouse et al. |
| 5,712,476 A | 1/1998 | Renfrew et al. |
| 5,733,729 A | 3/1998 | Lipshutz et al. |
| 5,741,640 A | 4/1998 | Fuller |
| 5,741,644 A | 4/1998 | Kambara et al. |
| 5,744,305 A | 4/1998 | Fodor et al. |
| 5,744,312 A | 4/1998 | Mamone et al. |
| 5,750,341 A | 5/1998 | Macevicz et al. |
| 5,753,788 A | 5/1998 | Fodor et al. |
| 5,755,943 A | 5/1998 | Middendorf et al. |
| 5,756,285 A | 5/1998 | Fuller |
| 5,759,014 A | 6/1998 | Van Lintel |
| 5,759,374 A | 6/1998 | Takahashi et al. |
| 5,762,876 A | 6/1998 | Lincoln et al. |
| 5,763,594 A | 6/1998 | Hiatt et al. |
| 5,776,767 A | 7/1998 | Stevens et al. |
| 5,776,782 A | 7/1998 | Tsuji |
| 5,789,168 A | 8/1998 | Leushner et al. |
| 5,795,722 A | 8/1998 | Lacroix et al. |
| 5,795,782 A | 8/1998 | Church et al. |
| 5,807,679 A | 9/1998 | Kamb |
| 5,808,045 A | 9/1998 | Hiatt et al. |
| 5,830,657 A | 11/1998 | Leushner et al. |
| 5,831,070 A | 11/1998 | Pease et al. |
| 5,832,165 A | 11/1998 | Reichert et al. |
| 5,834,758 A | 11/1998 | Trulson et al. |
| 5,836,750 A | 11/1998 | Cabuz |
| 5,837,832 A | 11/1998 | Chee et al. |
| 5,837,860 A | 11/1998 | Anderson et al. |
| 5,846,396 A | 12/1998 | Zanzucchi et al. |
| 5,846,727 A | 12/1998 | Soper et al. |
| 5,853,979 A | 12/1998 | Green et al. |
| 5,858,671 A | 1/1999 | Jones |
| 5,861,287 A | 1/1999 | Metzker et al. |
| 5,863,722 A | 1/1999 | Brenner |
| 5,872,244 A | 2/1999 | Hiatt et al. |
| 5,876,187 A | 3/1999 | Afromowitz et al. |
| 5,876,934 A | 3/1999 | Duthie et al. |
| 5,882,904 A | 3/1999 | Riedl et al. |
| 5,885,813 A | 3/1999 | Davis et al. |
| 5,889,165 A | 3/1999 | Fodor et al. |
| 5,902,723 A | 5/1999 | Dower et al. |
| 5,908,755 A | 6/1999 | Kumar et al. |
| 5,916,747 A | 6/1999 | Gilchrist et al. |
| 5,922,591 A | 7/1999 | Anderson et al. |
| 5,922,608 A | 7/1999 | Farnsworth et al. |
| 5,928,906 A | 7/1999 | Koster et al. |
| 5,928,919 A | 7/1999 | Reha-Krantz et al. |
| 5,945,283 A | 8/1999 | Kwok et al. |
| 5,945,284 A | 8/1999 | Livak et al. |
| 5,945,312 A | 8/1999 | Goodman et al. |
| 5,945,325 A | 8/1999 | Arnold et al. |
| 5,948,614 A | 9/1999 | Chatterjee |
| 5,952,174 A | 9/1999 | Nikiforov et al. |
| 5,954,932 A | 9/1999 | Takahashi et al. |
| 5,958,703 A | 9/1999 | Dower et al. |
| 5,959,781 A | 9/1999 | Kintz et al. |
| 5,959,837 A | 9/1999 | Yu |
| 5,965,446 A | 10/1999 | Ishikawa |
| 5,968,740 A | 10/1999 | Fodor et al. |
| 5,974,164 A | 10/1999 | Chee |
| 5,976,338 A | 11/1999 | Fujita et al. |
| 5,976,842 A | 11/1999 | Wurst |
| 5,981,186 A | 11/1999 | Gabe et al. |
| 5,981,956 A | 11/1999 | Stern |
| 5,994,058 A | 11/1999 | Senapathy |
| 5,994,085 A | 11/1999 | Cantor |
| 6,002,471 A | 12/1999 | Quake |
| 6,005,663 A | 12/1999 | Waterhouse et al. |
| 6,007,309 A | 12/1999 | Hartley |
| 6,015,714 A | 1/2000 | Baldarelli et al. |
| 6,017,702 A | 1/2000 | Lee et al. |
| 6,018,041 A | 1/2000 | Drmanac et al. |
| 6,020,457 A | 2/2000 | Klimash et al. |
| 6,024,925 A | 2/2000 | Little et al. |
| 6,025,136 A | 2/2000 | Drmanac |
| 6,028,190 A | 2/2000 | Mathies et al. |
| 6,030,782 A | 2/2000 | Anderson et al. |
| 6,043,080 A | 3/2000 | Lipshutz et al. |
| 6,046,005 A | 4/2000 | Ju et al. |

| | | | | | | |
|---|---|---|---|---|---|---|
| 6,049,380 | A | 4/2000 | Goodwin et al. | 6,309,701 | B1 | 10/2001 | Barbera-Guillem |
| 6,051,380 | A | 4/2000 | Sosnowski et al. | 6,309,824 | B1 | 10/2001 | Drmanac |
| 6,066,454 | A | 5/2000 | Lipshutz et al. | 6,309,836 | B1 | 10/2001 | Kwiatkowski |
| 6,071,394 | A | 6/2000 | Cheng et al. | 6,309,886 | B1 | 10/2001 | Ambrose et al. |
| 6,077,664 | A | 6/2000 | Slater et al. | 6,310,189 | B1 | 10/2001 | Fodor et al. |
| 6,077,674 | A | 6/2000 | Schleifer et al. | 6,312,893 | B1 | 11/2001 | Van Ness et al. |
| 6,087,095 | A | 7/2000 | Rosenthal et al. | 6,316,191 | B1 | 11/2001 | Drmanac et al. |
| 6,087,099 | A | 7/2000 | Gupte et al. | 6,322,968 | B1 | 11/2001 | Head et al. |
| 6,094,274 | A | 7/2000 | Yokoi | 6,331,439 | B1 | 12/2001 | Cherukuri et al. |
| 6,107,032 | A | 8/2000 | Kilger et al. | 6,333,183 | B1 | 12/2001 | Evans et al. |
| 6,107,044 | A | 8/2000 | Nikiforov | 6,335,824 | B1 | 1/2002 | Overbeck |
| 6,107,061 | A | 8/2000 | Johnson | 6,337,185 | B1 | 1/2002 | Asp et al. |
| 6,132,580 | A | 10/2000 | Mathies et al. | 6,337,188 | B1 | 1/2002 | Head et al. |
| 6,133,436 | A | 10/2000 | Koster et al. | 6,342,326 | B1 | 1/2002 | Milton |
| 6,136,212 | A | 10/2000 | Mastrangelo et al. | 6,344,325 | B1 | 2/2002 | Quake et al. |
| 6,136,962 | A | 10/2000 | Shi et al. | 6,346,379 | B1 | 2/2002 | Gelfand et al. |
| 6,140,053 | A | 10/2000 | Koster | 6,346,413 | B1 | 2/2002 | Fodor et al. |
| 6,140,494 | A | 10/2000 | Hamilton et al. | 6,355,420 | B1 | 3/2002 | Chan |
| 6,141,096 | A | 10/2000 | Stern et al. | 6,355,432 | B1 | 3/2002 | Fodor et al. |
| 6,143,151 | A | 11/2000 | Middendorf et al. | 6,361,671 | B1 | 3/2002 | Mathies et al. |
| 6,147,205 | A | 11/2000 | McGall et al. | 6,361,937 | B1 | 3/2002 | Stryer |
| 6,156,501 | A | 12/2000 | McGall et al. | 6,368,562 | B1 | 4/2002 | Yao |
| 6,165,694 | A | 12/2000 | Liu | 6,368,699 | B1 | 4/2002 | Gilbert et al. |
| 6,177,249 | B1 | 1/2001 | Kwok et al. | 6,383,749 | B2 | 5/2002 | Bochkariov et al. |
| 6,197,506 | B1 | 3/2001 | Fodor et al. | 6,387,626 | B1 | 5/2002 | Shi et al. |
| 6,197,595 | B1 | 3/2001 | Anderson et al. | 6,395,232 | B1 | 5/2002 | McBride |
| 6,207,381 | B1 | 3/2001 | Larsson et al. | 6,395,559 | B1 | 5/2002 | Swenson |
| 6,207,960 | B1 | 3/2001 | Stern | 6,397,150 | B1 | 5/2002 | Izmailov |
| 6,210,896 | B1 | 4/2001 | Chan | 6,399,364 | B1 | 6/2002 | Reeve et al. |
| 6,214,246 | B1 | 4/2001 | Craighead | 6,401,267 | B1 | 6/2002 | Drmanac |
| 6,214,987 | B1 | 4/2001 | Hiatt et al. | 6,403,311 | B1 | 6/2002 | Chan |
| 6,221,592 | B1 | 4/2001 | Schwartz et al. | 6,403,315 | B1 | 6/2002 | Drmanac |
| 6,221,654 | B1 | 4/2001 | Quake et al. | 6,403,317 | B1 | 6/2002 | Anderson |
| 6,225,052 | B1 | 5/2001 | Batz et al. | 6,403,320 | B1 | 6/2002 | Read et al. |
| 6,225,062 | B1 | 5/2001 | Dunn et al. | 6,403,957 | B1 | 6/2002 | Fodor et al. |
| 6,225,092 | B1 | 5/2001 | Kilger et al. | 6,404,907 | B1 | 6/2002 | Gilchrist et al. |
| 6,225,109 | B1 | 5/2001 | Juncosa et al. | 6,406,893 | B1 | 6/2002 | Knapp et al. |
| 6,225,567 | B1 | 5/2001 | Kester | 6,407,858 | B1 | 6/2002 | Montagu |
| 6,225,625 | B1 | 5/2001 | Pirrung et al. | 6,408,878 | B2 | 6/2002 | Unger et al. |
| 6,228,593 | B1 | 5/2001 | Lipshutz et al. | 6,416,952 | B1 | 7/2002 | Pirrung et al. |
| 6,232,075 | B1 | 5/2001 | Williams | 6,420,169 | B1 | 7/2002 | Read et al. |
| 6,232,103 | B1 | 5/2001 | Short | 6,423,273 | B1 | 7/2002 | O'Mara |
| 6,235,465 | B1 | 5/2001 | Kolberg et al. | 6,432,634 | B1 | 8/2002 | Digby et al. |
| 6,235,473 | B1 | 5/2001 | Friedman et al. | 6,436,641 | B1 | 8/2002 | Izmailov |
| 6,242,180 | B1 | 6/2001 | Chee | 6,436,646 | B1 | 8/2002 | Nikiforov |
| 6,242,528 | B1 | 6/2001 | Clark et al. | 6,440,664 | B1 | 8/2002 | Digby et al. |
| 6,245,506 | B1 | 6/2001 | Laugharn, Jr. et al. | 6,440,722 | B1 | 8/2002 | Knapp et al. |
| 6,245,507 | B1 | 6/2001 | Bogdanov | 6,444,106 | B1 | 9/2002 | Mcbride et al. |
| 6,245,518 | B1 | 6/2001 | Baier | 6,444,173 | B1 | 9/2002 | Sjursen et al. |
| 6,251,610 | B1 | 6/2001 | Gupte et al. | 6,444,424 | B1 | 9/2002 | Chatterjee et al. |
| 6,255,083 | B1 | 7/2001 | Williams | 6,444,461 | B1 | 9/2002 | Knapp et al. |
| 6,255,475 | B1 | 7/2001 | Kwiatkowski | 6,447,724 | B1 | 9/2002 | Jensen et al. |
| 6,258,533 | B1 | 7/2001 | Jones | 6,448,090 | B1 | 9/2002 | McBride |
| 6,261,775 | B1 | 7/2001 | Bastian et al. | 6,451,536 | B1 | 9/2002 | Fodor et al. |
| 6,261,776 | B1 | 7/2001 | Pirrung et al. | 6,479,267 | B1 | 11/2002 | Davis et al. |
| 6,261,848 | B1 | 7/2001 | Anderson et al. | 6,485,690 | B1 | 11/2002 | Pfost et al. |
| 6,262,838 | B1 | 7/2001 | Montagu | 6,485,909 | B1 | 11/2002 | Hong et al. |
| 6,263,286 | B1 | 7/2001 | Gilmanshin et al. | 6,485,944 | B1 | 11/2002 | Church et al. |
| 6,268,152 | B1 | 7/2001 | Fodor et al. | 6,495,363 | B2 | 12/2002 | Bogdanov |
| 6,268,219 | B1 | 7/2001 | Mcbride et al. | 6,506,560 | B1 | 1/2003 | Hughes et al. |
| 6,269,846 | B1 | 8/2001 | Overbeck et al. | 6,511,803 | B1 | 1/2003 | Church et al. |
| 6,270,644 | B1 | 8/2001 | Mathies et al. | 6,514,706 | B1 | 2/2003 | Von Kalle et al. |
| 6,270,961 | B1 | 8/2001 | Drmanac | 6,521,428 | B1 | 2/2003 | Senapathy |
| 6,274,320 | B1 | 8/2001 | Rothberg et al. | 6,524,829 | B1 | 2/2003 | Seeger |
| 6,274,351 | B1 | 8/2001 | Peponnet | 6,528,258 | B1 | 3/2003 | Russell |
| 6,277,604 | B1 | 8/2001 | Peponnet | 6,528,288 | B2 | 3/2003 | Senapathy |
| 6,280,954 | B1 | 8/2001 | Ulfendahl | 6,537,755 | B1 | 3/2003 | Drmanac |
| 6,284,460 | B1 | 9/2001 | Fodor et al. | 6,537,757 | B1 | 3/2003 | Langmore et al. |
| 6,287,821 | B1 | 9/2001 | Shi et al. | 6,546,340 | B2 | 4/2003 | Lipshutz et al. |
| 6,294,336 | B1 | 9/2001 | Boyce-Jacino et al. | 6,551,784 | B2 | 4/2003 | Fodor et al. |
| 6,294,337 | B1 | 9/2001 | Hayashizaki | 6,551,817 | B2 | 4/2003 | Besemer et al. |
| 6,306,607 | B2 | 10/2001 | Williams | 6,554,987 | B1 | 4/2003 | Gilchrist et al. |
| 6,309,601 | B1 | 10/2001 | Juncosa et al. | 6,555,349 | B1 | 4/2003 | O'Donnell |

| | | |
|---|---|---|
| 6,558,945 B1 | 5/2003 | Kao |
| 6,562,566 B1 | 5/2003 | Hoheisel |
| 6,566,059 B1 | 5/2003 | Stanton, Jr. et al. |
| 6,566,515 B1 | 5/2003 | McGall et al. |
| 6,573,047 B1 | 6/2003 | Hung et al. |
| 6,573,374 B1 | 6/2003 | Muehlegger et al. |
| 6,576,424 B2 | 6/2003 | Fodor et al. |
| 6,576,425 B2 | 6/2003 | McGall et al. |
| 6,579,704 B2 | 6/2003 | Short |
| 6,582,923 B2 | 6/2003 | Stanton, Jr. et al. |
| 6,585,939 B1 | 7/2003 | Dapprich |
| 6,607,888 B2 | 8/2003 | Schwartz et al. |
| 6,610,482 B1 | 8/2003 | Fodor et al. |
| 6,613,513 B1 | 9/2003 | Parce et al. |
| 6,623,928 B2 | 9/2003 | Van Ness et al. |
| 6,627,748 B1 | 9/2003 | Ju et al. |
| 6,632,655 B1 | 10/2003 | Mehta et al. |
| 6,642,001 B1 | 11/2003 | Bolk et al. |
| 6,664,079 B2 | 12/2003 | Ju et al. |
| 6,719,868 B1 | 4/2004 | Schueller et al. |
| 6,750,018 B2 | 6/2004 | Kambara et al. |
| 6,762,048 B2 | 7/2004 | Williams |
| 6,780,591 B2 | 8/2004 | Williams et al. |
| 6,783,938 B2 | 8/2004 | Nygren et al. |
| 6,787,308 B2 | 9/2004 | Balasubramanian et al. |
| 6,818,395 B1 | 11/2004 | Quake et al. |
| 6,908,736 B1 | 6/2005 | Densham |
| 6,911,345 B2 | 6/2005 | Quake et al. |
| 2001/0024890 A1 | 9/2001 | Kambara et al. |
| 2001/0044531 A1 | 11/2001 | McGall et al. |
| 2001/0046681 A1 | 11/2001 | Senapathy |
| 2002/0009744 A1 | 1/2002 | Bogdanov |
| 2002/0012910 A1 | 1/2002 | Weiss et al. |
| 2002/0015961 A1 | 2/2002 | Kwiatkowski |
| 2002/0025529 A1 | 2/2002 | Quake et al. |
| 2002/0032320 A1 | 3/2002 | Burgess et al. |
| 2002/0034792 A1 | 3/2002 | Kilger et al. |
| 2002/0039738 A1 | 4/2002 | Williams et al. |
| 2002/0042112 A1 | 4/2002 | Koster et al. |
| 2002/0045182 A1 | 4/2002 | Singh et al. |
| 2002/0051992 A1 | 5/2002 | Bridgham et al. |
| 2002/0053532 A1 | 5/2002 | Quaker et al. |
| 2002/0061529 A1 | 5/2002 | Bridgham et al. |
| 2002/0072055 A1 | 6/2002 | Jones |
| 2002/0086318 A1 | 7/2002 | Manalis et al. |
| 2002/0102586 A1 | 8/2002 | Ju et al. |
| 2002/0102595 A1 | 8/2002 | Davis |
| 2002/0106673 A1 | 8/2002 | Drmanac et al. |
| 2002/0115076 A1 | 8/2002 | Williams |
| 2002/0115092 A1 | 8/2002 | Rebek, Jr. |
| 2002/0119484 A1 | 8/2002 | Weidenhammer et al. |
| 2002/0123046 A1 | 9/2002 | Smith et al. |
| 2002/0137046 A1 | 9/2002 | Koster |
| 2002/0137052 A1 | 9/2002 | Bridgham et al. |
| 2002/0137062 A1 | 9/2002 | Williams et al. |
| 2002/0138205 A1 | 9/2002 | Miller et al. |
| 2002/0142329 A1 | 10/2002 | Matray et al. |
| 2002/0142333 A1 | 10/2002 | Gelfand et al. |
| 2002/0146704 A1 | 10/2002 | Head et al. |
| 2002/0146726 A1 | 10/2002 | Matray et al. |
| 2002/0150903 A1 | 10/2002 | Koster |
| 2002/0150938 A1 | 10/2002 | Kneipp et al. |
| 2002/0164629 A1 | 11/2002 | Quake et al. |
| 2002/0168642 A1 | 11/2002 | Drukier |
| 2002/0168678 A1 | 11/2002 | Williams et al. |
| 2002/0172948 A1 | 11/2002 | Perlin |
| 2002/0177129 A1 | 11/2002 | Paabo et al. |
| 2002/0182601 A1 | 12/2002 | Sampson et al. |
| 2002/0192661 A1 | 12/2002 | Paabo et al. |
| 2002/0192662 A1 | 12/2002 | Boyce-Jacino et al. |
| 2002/0192691 A1 | 12/2002 | Drmanac |
| 2002/0197618 A1 | 12/2002 | Sampson |
| 2003/0003272 A1 | 1/2003 | Laguitton |
| 2003/0003498 A1 | 1/2003 | Digby et al. |
| 2003/0008285 A1 | 1/2003 | Fischer |
| 2003/0008413 A1 | 1/2003 | Kim et al. |
| 2003/0017461 A1 | 1/2003 | Singh et al. |
| 2003/0022207 A1 | 1/2003 | Balasubramanian et al. |
| 2003/0027140 A1 | 2/2003 | Ju et al. |
| 2003/0036080 A1 | 2/2003 | Jensen et al. |
| 2003/0044778 A1 | 3/2003 | Goelet et al. |
| 2003/0044779 A1 | 3/2003 | Goelet et al. |
| 2003/0044781 A1 | 3/2003 | Korlach et al. |
| 2003/0044816 A1 | 3/2003 | Denison et al. |
| 2003/0054181 A1 | 3/2003 | Swerdlow et al. |
| 2003/0054361 A1 | 3/2003 | Heller |
| 2003/0058440 A1 | 3/2003 | Scott et al. |
| 2003/0058799 A1 | 3/2003 | Yamakawa et al. |
| 2003/0059778 A1 | 3/2003 | Berlin et al. |
| 2003/0060431 A1 | 3/2003 | Simmonds et al. |
| 2003/0064366 A1 | 4/2003 | Hardin et al. |
| 2003/0064398 A1 | 4/2003 | Barnes |
| 2003/0064483 A1 | 4/2003 | Shaw et al. |
| 2003/0087237 A1 | 5/2003 | Hong et al. |
| 2003/0087300 A1 | 5/2003 | Knapp et al. |
| 2003/0092005 A1 | 5/2003 | Levene et al. |
| 2003/0092007 A1 | 5/2003 | Gibbs et al. |
| 2003/0096258 A1 | 5/2003 | Fu et al. |
| 2003/0100006 A1 | 5/2003 | Senapathy |
| 2003/0104437 A1 | 6/2003 | Barnes et al. |
| 2003/0104466 A1 | 6/2003 | Knapp et al. |
| 2003/0108867 A1 | 6/2003 | Chee et al. |
| 2003/0138809 A1 | 7/2003 | Williams et al. |
| 2003/0148344 A1 | 8/2003 | Rothberg et al. |
| 2003/0162213 A1 | 8/2003 | Fuller et al. |
| 2003/0186227 A1 | 10/2003 | Balasubramanian et al. |
| 2003/0186255 A1 | 10/2003 | Williams et al. |
| 2003/0190627 A1 | 10/2003 | Zhao et al. |
| 2003/0190647 A1 | 10/2003 | Odera |
| 2003/0190663 A1 | 10/2003 | Yang et al. |
| 2003/0194722 A1 | 10/2003 | Odedra et al. |
| 2003/0194740 A1 | 10/2003 | Williams |
| 2003/0215862 A1 | 11/2003 | Wallace et al. |
| 2004/0009487 A1 | 1/2004 | Kadushin et al. |
| 2004/0014096 A1 | 1/2004 | Anderson et al. |
| 2004/0029115 A9 | 2/2004 | Dower et al. |
| 2004/0038206 A1 | 2/2004 | Zhang et al. |
| 2004/0054162 A1 | 3/2004 | Hanna |
| 2004/0106110 A1 | 6/2004 | Balasubramanian et al. |
| 2004/0110162 A1 | 6/2004 | Lapidus et al. |
| 2004/0126770 A1 | 7/2004 | Kumar et al. |
| 2005/0014175 A1 | 1/2005 | Quake et al. |
| 2005/0100932 A1 | 5/2005 | Lapidus et al. |
| 2005/0147992 A1 | 7/2005 | Quake et al. |
| 2005/0170367 A1 | 8/2005 | Quake et al. |
| 2005/0239085 A1 | 10/2005 | Buzby et al. |
| 2006/0147935 A1* | 7/2006 | Linnarsson ............. 435/6 |

FOREIGN PATENT DOCUMENTS

| | | |
|---|---|---|
| EP | 0223618 A2 | 5/1987 |
| EP | 0412883 A1 | 2/1991 |
| EP | 0481065 | 4/1992 |
| EP | 0579997 A1 | 1/1994 |
| EP | 0703364 A1 | 3/1996 |
| EP | 0706004 A2 | 4/1996 |
| EP | 0779436 A2 | 6/1997 |
| EP | 0845603 A1 | 6/1998 |
| EP | 0932700 B1 | 8/1999 |
| EP | 0946752 B1 | 10/1999 |
| EP | 0955085 A2 | 11/1999 |
| EP | 0999055 A2 | 5/2000 |
| EP | 0706004 B1 | 8/2003 |
| GB | 2155152 A | 9/1985 |
| GB | 2308460 A | 6/1997 |
| GB | 2400518 A | 10/2004 |

| | | | | | | |
|---|---|---|---|---|---|---|
| SE | 9500589 | 2/1995 | | WO | 99/64840 A1 | 12/1999 |
| WO | 89/03432 A1 | 4/1989 | | WO | 99/65938 A2 | 12/1999 |
| WO | 89/09283 A1 | 10/1989 | | WO | 99/66076 A1 | 12/1999 |
| WO | 90/13666 A1 | 11/1990 | | WO | 99/66313 A1 | 12/1999 |
| WO | 90/15070 A1 | 12/1990 | | WO | 00/00637 A2 | 1/2000 |
| WO | 91/06678 A1 | 5/1991 | | WO | 00/06770 A1 | 2/2000 |
| WO | 92/10092 A1 | 6/1992 | | WO | 00/09753 A1 | 2/2000 |
| WO | 92/10587 A1 | 6/1992 | | WO | 00/11223 A1 | 3/2000 |
| WO | 93/05183 A1 | 3/1993 | | WO | 00/17397 A1 | 3/2000 |
| WO | 93/06121 A1 | 4/1993 | | WO | 00/26935 A2 | 5/2000 |
| WO | 93/21340 A1 | 10/1993 | | WO | 00/34523 A1 | 6/2000 |
| WO | 95/12608 A1 | 5/1995 | | WO | 00/37680 A1 | 6/2000 |
| WO | 95/27080 A1 | 10/1995 | | WO | 00/40750 A1 | 7/2000 |
| WO | 96/04547 A1 | 2/1996 | | WO | 00/40758 A2 | 7/2000 |
| WO | 96/12014 A1 | 4/1996 | | WO | 00/42223 A1 | 7/2000 |
| WO | 96/12039 A1 | 4/1996 | | WO | 00/43540 A1 | 7/2000 |
| WO | 96/27025 A1 | 9/1996 | | WO | 00/43752 A1 | 7/2000 |
| WO | 97/02488 A1 | 1/1997 | | WO | 00/50642 A1 | 8/2000 |
| WO | 97/22076 A1 | 6/1997 | | WO | 00/53805 A1 | 9/2000 |
| WO | 97/23650 A2 | 6/1997 | | WO | 00/53812 A2 | 9/2000 |
| WO | 97/37041 A2 | 10/1997 | | WO | 00/56937 A2 | 9/2000 |
| WO | 97/39150 A1 | 10/1997 | | WO | 00/58507 A1 | 10/2000 |
| WO | 97/40184 A1 | 10/1997 | | WO | 00/58516 A2 | 10/2000 |
| WO | 97/41258 A1 | 11/1997 | | WO | 00/68410 A1 | 11/2000 |
| WO | 97/41259 A1 | 11/1997 | | WO | 00/70073 A1 | 11/2000 |
| WO | 97/42348 A1 | 11/1997 | | WO | 00/71755 A2 | 11/2000 |
| WO | 98/00708 A1 | 1/1998 | | WO | 00/79007 A1 | 12/2000 |
| WO | 98/02575 A1 | 1/1998 | | WO | 01/001025 A3 | 1/2001 |
| WO | 98/03684 A1 | 1/1998 | | WO | 01/16375 A2 | 3/2001 |
| WO | 98/07069 A1 | 2/1998 | | WO | 01/23610 A2 | 4/2001 |
| WO | 98/13523 A1 | 4/1998 | | WO | 01/24937 A2 | 4/2001 |
| WO | 98/08978 A1 | 5/1998 | | WO | 01/25480 A2 | 4/2001 |
| WO | 98/20019 A1 | 5/1998 | | WO | 01/31055 A2 | 5/2001 |
| WO | 98/20020 A2 | 5/1998 | | WO | 01/32930 A1 | 5/2001 |
| WO | 98/20166 A2 | 5/1998 | | WO | 01/38574 A1 | 5/2001 |
| WO | 98/21361 A1 | 5/1998 | | WO | 01/48184 A2 | 5/2001 |
| WO | 98/27228 A1 | 6/1998 | | WO | 01/42496 A2 | 6/2001 |
| WO | 98/28440 A1 | 7/1998 | | WO | 01/57248 A2 | 8/2001 |
| WO | 98/33939 A1 | 8/1998 | | WO | 01/57249 A1 | 8/2001 |
| WO | 98/40520 A1 | 9/1998 | | WO | 01/61044 A1 | 8/2001 |
| WO | 98/41650 A2 | 9/1998 | | WO | 01/64838 A2 | 9/2001 |
| WO | 98/41657 A1 | 9/1998 | | WO | 01/75154 A2 | 10/2001 |
| WO | 98/44152 A1 | 10/1998 | | WO | 01/79536 A1 | 10/2001 |
| WO | 98/45481 A1 | 10/1998 | | WO | 01/85991 A2 | 11/2001 |
| WO | 98/53300 A2 | 11/1998 | | WO | 01/92284 A1 | 12/2001 |
| WO | 98/54669 A1 | 12/1998 | | WO | 01/96607 A2 | 12/2001 |
| WO | 98/55593 A1 | 12/1998 | | WO | 02/00343 A2 | 1/2002 |
| WO | 99/01768 A1 | 1/1999 | | WO | 02/02584 A1 | 1/2002 |
| WO | 99/05221 A1 | 2/1999 | | WO | 02/02795 A2 | 1/2002 |
| WO | 99/05315 A2 | 2/1999 | | WO | 02/02813 A2 | 1/2002 |
| WO | 99/06422 A2 | 2/1999 | | WO | 02/03305 A2 | 1/2002 |
| WO | 99/13109 A1 | 3/1999 | | WO | 02/04680 A2 | 1/2002 |
| WO | 99/13110 A1 | 3/1999 | | WO | 02/20836 A2 | 3/2002 |
| WO | 99/09616 A1 | 4/1999 | | WO | 02/20837 A2 | 3/2002 |
| WO | 99/17093 A1 | 4/1999 | | WO | 02/27032 A1 | 4/2002 |
| WO | 99/19516 A1 | 4/1999 | | WO | 02/29106 A2 | 4/2002 |
| WO | 99/24797 A1 | 5/1999 | | WO | 02/30486 A3 | 4/2002 |
| WO | 99/27137 A1 | 6/1999 | | WO | 02/35441 A2 | 5/2002 |
| WO | 99/31278 A1 | 6/1999 | | WO | 02/36832 A2 | 5/2002 |
| WO | 99/37810 A1 | 7/1999 | | WO | 02/44414 A2 | 6/2002 |
| WO | 99/39001 A2 | 8/1999 | | WO | WO 02/244425 A2 | 6/2002 |
| WO | 99/40105 A2 | 8/1999 | | WO | 02/061126 A2 | 8/2002 |
| WO | 99/40223 A1 | 8/1999 | | WO | 02/061127 A2 | 8/2002 |
| WO | 99/41410 A1 | 8/1999 | | WO | 02/072779 A2 | 9/2002 |
| WO | 00/30591 A1 | 9/1999 | | WO | 02/072892 A2 | 9/2002 |
| WO | 99/44045 A1 | 9/1999 | | WO | 02/077694 A1 | 10/2002 |
| WO | 99/45153 A2 | 9/1999 | | WO | 02/079519 A1 | 10/2002 |
| WO | 99/47539 A1 | 9/1999 | | WO | 02/088381 A2 | 11/2002 |
| WO | 99/47706 A1 | 9/1999 | | WO | 02/088382 A2 | 11/2002 |
| WO | 99/53423 A1 | 10/1999 | | WO | 02/097113 A2 | 12/2002 |
| WO | 99/57321 A1 | 11/1999 | | WO | 02/099398 A1 | 12/2002 |
| WO | 99/61888 A2 | 12/1999 | | WO | 03/002767 A1 | 1/2003 |
| WO | 99/64437 A1 | 12/1999 | | WO | 03/016565 A2 | 2/2003 |

| | | | |
|---|---|---|---|
| WO | 03/020895 A2 | 3/2003 | |
| WO | 03/020968 A2 | 3/2003 | |
| WO | 03/021010 A2 | 3/2003 | |
| WO | 03/031947 A2 | 4/2003 | |
| WO | 03/044678 A1 | 5/2003 | |
| WO | 03/048178 A2 | 6/2003 | |
| WO | 03/048991 A2 | 6/2003 | |
| WO | 03/062897 A1 | 7/2003 | |
| WO | 03/106642 A2 | 12/2003 | |
| WO | 2004/061119 A2 | 7/2004 | |
| WO | 2004/074503 A2 | 9/2004 | |
| WO | 2005/047523 A2 | 5/2005 | |
| WO | 2005/080605 A2 | 9/2005 | |

OTHER PUBLICATIONS

Adam et al., "Individual genomes targeted in sequencing revolution", *Nature*, vol. 411, p. 402 (May 2001).

Agrawal, S. et al., "Site Specific Functionalization of Oligodeoxynucleotides for Non-Radioactive Labelling", *Tetrahedron Letters*, vol. 31, No. 11, pp. 1543-1546 (1990).

Ambrose, W. et al., "Single Molecule Detection With Total Internal Reflection Excitation: Comparing Signal-to-Background and Total Signals in Different Geometries", *Cytometry*, vol. 36, pp. 224-231 (1999).

Amit, B. et al., "Photosensitive Protecting Groups of Amino Sugars and Their Use in Glycoside Synthesis ... Derivatives", 1. *Org. Chem.*, 39(2):192-6 (1974).

Arndt-Jovin, D. et al., "Immunofluorescence Localization of Z-DNA in Chromosomes: Quantitation by Scanning Microphotometry and Computer-assisted Image Analysis", 1. *The Journal of Cell Biology*, vol. 101, pp. 1422-1433, (Oct. 1985).

Augustin, M.A., W. Ankenbauer, and B. Angerer, "Progress towards single-molecule sequencing: enzymatic synthesis of nucleotide-specifically labled DNA." *Journal of Biotechnology*, 8(13):289-301 (2001).

Axelrod, D., "Cell-Substrate Contacts Illuminated by Total Internal Reflection Fluorescence", 1. *The Journal of Cell Biology*, vol. 89, pp. 141-145, (Apr. 1981).

Axelrod, D. et al., "Total internal reflection fluorescent microscopy", *J Microscopy*, vol. 129, pp. 19-28, (1983).

Bai, X., et al., "Photocleavage of a 2-nitrobenzyl linker bridging a fluorophore to the 5' end of DNA." *Proc Natl Acad Sci USA*, 2003, vol. 100(2). p. 409-13.

Basche, T. et al., "Single Molecule Optical Detection, Imaging and Spectroscopy", Chs. 2 and 3, Weinheim:VCM, Germany (1997).

Beaucage, S. et al., "Advances in the Synthesis of Oligonucleotides by the Phosphoramidite Approach" *Tetrahedron*, 48:2223-2311 (1992).

Beese, L. et al., "Structure of DNA Polymerase I Klenow Fragment Bound to Duplex DNA", *Science*, 260:352-355 (1993).

Bennett et. al., "Solexa Sequencing Chemistry can be applied to different platforms which will have common elements in detection and data processing", *Pharmacogenomics* 5(4), pp. 433-438, (2004).

Biesalski et al., "Preparation and Characterization of a Polyelectrolyte Monolayer Covalently Attached to a Planar Solid Surface", *Macromolecules* 111, 32, 2309-2316. Article was published on the web Mar. 10, 1999.

Black, D.L., "Protein diversity from alternating splicing: A challenge for bioinformatics and post genome biology", *Cell*, 2000. 103(3): p. 367-370.

Blattner, F.R., et al., "The Complete genome sequence of *Escherichia coli* K-12.", *Science*, 277: 1453-74 (1997).

Boles et. al., "High-Resolution Mapping of Carcinogen Binding Sites on DNA", *Biochemistry*, 1986, 25, 3039-3043.

Brakmann, S. and P. Nieckchen, "The large fragment of *Escherichia coli* DNA polymerase I can synthesize DNA exclusively from fluorescently labled nucleotides." *Chembiochem*, 2(10):773-777 (2001).

Brakmann et. al, "Optimal Enzymes for Single-Molecule Sequencing", *Current Pharmaceutical Biotechnology*, 5, pp. 119-126 (2004).

Braslavsky, I. et al., "Sequence information can be obtained from single DNA molecules", *PNAS*, vol. 100, No. 7, pp. 3960-3964 (Apr. 2003).

Braslavsky, I. et al., "Objective-type dark-field illumination for scattering from microbeads", *Applied Optics*, vol. 40, No. 31, pp. 5650-5657, (Nov. 2001).

Braslavsky, I. et al., "Single Molecule Measurements of DNA Polymerase Activity: A Step Towards Single Molecule Sequencing", *Biophys.* 1. *Abstracts*, p. 507A (2002).

Brechtel, R. et al., "Control of the electro osmotic flow by metal-salt-containing buffers",*J Chromatoraphy A*, vol. 716, pp. 97-105, (1995).

Bridgman, A. et al., "An improved method for the synthesis of mercurated dUTP. Enzymatic synthesis of Hg-labelled DNA of high molecular weight suitable for use in an image based DNA sequencing strategy", *DNA Seq.*, vol. 6, No. 4, pp. 199-209 (1996).

Bruggert, J. "Microfabricated tools for nanoscience", *J. Micromech. Microeng.*, 3, pp. 161-167 (1993).

Bryzek, J. et al., "Micromachines on the march", *IEEE Spectrum*, vol. 31, No. 5, pp. 20-31, (1994).

Buchaillot, L. et al., "Silicon Nitride Thin Films Young's Modulus Determination by an Optical Non Destructive Method", *Jpn. J. Appl. Phys.*, vol. 36, pp. L794-L797, (Jun. 1997).

Burghardt, T. et al., "Total Internal Reflection Fluorescence Study of Energy Transfer in Surface-Adsorbed and Dissolved Bovine Serum Albumin", *Biochemistry*, vol. 22, pp. 979-985 (1983).

Burghardt, et al., "Total Internal Reflection/Fluorescence Photobleaching Recovery Study of Serum Albumin Adsorption Dynamics", *Biophys. Journal*, vol. 33, pp. 455-468 (Mar. 1981).

Butler, D. "Draft data leave geneticists with a mountain still to climb", *Nature*, vol. 405, Issue 6782, pp. 984-985 (May 2000).

Canard, B., B. Cardona, and R.S. Sarfati, "Catalytic editing properties of DNA polymerases," *Proc Natl Acad Sci USA*, 92(24): p. 10859-63 (1995).

Canard, et al., "DNA polymerase fluorescent substrates with reversible 3'-tags", *Gene*, 148(1): 1-6 (1994).

Cheng et al., "High-speed DNA sequence analysis," *Prog. in Biochem. and Biophys.*, vol. 22, pp. 223-227 (1995).

Chicurel, M., "Faster, better, cheaper genotyping", *Nature*, vol. 412, Issue 6847, pp. 580-582, (Aug. 2001).

Chidgeavadze et al., '2',3'-Dideoxy-3' aminonucleoside 5'-triphosphates are the terminators of DNA synthesis catalyzed by DNA polymerases, *Nuc. Acids Res.*, 12(3):1671-1686 (1984).

Chidgeavadze, Z. et al., "3'-Fluro-2',3'-dideoxyribonucleoside 5'-triphosphates: terminators of DNA synthesis", *FEBS Letters*, 183(2):275-278 (1985).

Chiu, D. et al., "Patterned deposition of cells and proteins onto surfaces by using three-dimensional microfluidic systems," *PNAS*, vol. 97, No. 6, pp. 2408-2413 (2000).

Chou et al., "A microfabricated device for sizing and sorting DNA molecules", Applied Sciences, Biophysics: Proc. Natl. Acad. Sci. USA 96, pp. 11-13 (1999).

Chou et al., "A Microfabricated Rotary Pump", Biomedical Microdevices. vol. 3: p. 323-330 (2001).

Close, D. et al., "Ultraviolet Photobleaching of Free Radicals Created in y-Irradiated Amino Acids", *Radiation Research*, vol. 53, pp. 349-357 (1973).

Cooper, J. et al., "Analysis of Fluorescence Energy Transfer in Duplex and Branched DNA Molecules", *Biochemistry*, vol. 29, pp. 9261-9268 (1990).

Crocker, J.C. and D.G. Grier, "Methods of digital video microscopy for colloidal studies." *Journal of Colloid and Interface Science*, 179(1): p. 298-310 (1996).

Dapprich, J., "Single-molecule DNA digestion by lambda-exonuclease." *Cytometry*, 36(3): p. 163-168 (1999).

Debenham, J.S., et al., "Two New Orthogonal Amine-Protecting Groups that can be Cleaved under Mild or Neutral Conditions." *Journal of the American Chemical Society*, 117(11): p. 3302-3 (1995).

Decher, G. et al. "Buildup of ultrathin multiplayer films by a self-assembly process: III. Consecutively alternating absorption of anionic and cationic polyelectrolytes in charged surfaces", *Thin Solid Films*, 210:831-835 (1992).

Decher G.; et al., "Fuzzy nanoassemblies : Toward layered polymeric multicomposites." *Science*, 277(5330): p. 1232-1237 (1997).

Delamarche, E. et al., "Patterned Delivery of Immunoglobulins to Surfaces Using Microfluidic Networks", *Science* 276:779-781 (1997).

Dickson et al., "Simultaneous Imaging of Individual Molecules aligned both parallel and perpendicular to the optic axis", *The American Physical Society*, vol. 81, No. 24, pp. 5322-5325 (1998).

Doktycz, M. et al., "Genosensors and Model Hybridization Studies", *Automation Technologies for Genome Characterization*, Ch. 10 T. Beugelsdijk (Ed), John Wiley & Sons, Inc., pp. 205-225 (1997).

Doublie, S. et al., "Crystal structure of a bacteriophage T7 DNA replication complex at 2.2 A resolution", *Nature*, vol. 391, pp. 251-258 (Jan. 1998).

Driscoll et al., "Atomic-Scale Imaging of DNA Using Scanning Tunneling Microscopy." *Nature*, 346(6281): p. 294-296 (1990).

Drmanac, R. et al., "Sequencing by hybridization: Towards an automated sequencing of one million M13 clones arrayed on membranes", *Electrophoresis*, 13:566-573 (1992).

Duffy et al., "Patterning Electroluminescence Materials with Feature Sizes as Small as 5 um Using Elastomeric Membranes as Masks for Dry Lift-Off," *Advanced Materials* vol. 11, No. 7, pp. 546-552 (1999).

Duffy et al., "Rapid prototyping of microfluidic switches in poly(dimethyl siloxane) and their acuation by electroosmotic flow," *J. Micromech. Microeng.*, vol. 9, pp. 211-217 (1999).

Duffy et al., "Rapid Prototyping of Microfluidic Systems in Poly(dimethylsiloxane)", *Analytical Chemistry*, vol. 70, No. 23, pp. 4974-4984 (1998).

Effenhauser et al., "Integrated capillary electrophoresis on Flexible silicone microdevices: Analysis of DNA restriction fragments and detection of single DNA molecules on microchips," *Anal. Chem.*, vol. 69, pp. 3451-3457 (1997).

Effenhauser et al., "Integrated chip-based capillary electrophoresis," *Electrophoresis*, vol. 18, pp. 2203-2213 (1997).

Eigen, M. et al., "Sorting single molecules: Application to diagnostics and evolutionary biotechnology", *PNAS*, vol. 91, pp. 5740-5747, (Jun. 1994).

Evangelista, R.A., et al. "Characterization of fluorescent nucleoside triphosphates by capillary electrophoresis with laser-induced fluorescence detection: action of alkaline phosphatase and DNA polymerase." *Analytical Biochemistry*, 235(1): p. 89-97 (1996).

Fahrenberg et al., "A microvalve system fabricated by thermoplastic molding," *J. Micromech. Microeng.*, vol. 5, pp. 169-171(1995).

Ferguson, et al., "A fiber-optic DNA biosensor microarray for the analysis of gene expression," *Nature Biotechnology*, vol. 14, pp. 1681-1684 (1996).

Forster, T., "Delocalized Excitation and Excitation Transfer", Modern Quantum Chem., *Istanbul Lectures*, Part TII, pp. 93-137, Academic Press, New York (1965).

Fritz, I. et al., "Electronic detection of DNA by its intrinsic molecular charge", *PNAS*, vol. 99, No. 22, pp. 14142-14146 (Oct. 2002).

Fu et al., "A microfabricated fluorescence-activated cell sorter," *Nature Biotechnology*, vol. 17, pp. 1109-1111 (1999).

Fu e al., "An integrated microfabricated cell sorter", *Analytical Chemistry*, 74(11): pp. 2451-2457 (2002).

Funatsu, T. et al., "Imaging of single fluorescent molecules and individual ATP turnovers by single myosin molecules in aqueous solution", *Nature*, vol. 374, pp. 555-559 (Apr. 1995).

Garcia, A., "Determination of Ion Penneability by Fluorescence Quenching", *Meth. in Enzymology*, 207:501-511 (1992).

Gardner, A., et al., "Acyclic and dideoxy terminator preferences denote divergent sugar recognition by archaeon and *Taq* DNA polymerases", *Nucleic Acids Research*, vol. 30, No. 2, pp. 605-613 (2002).

Gardner et al., "Comparative kinetics of nucleotide analog incorporation by Vent DNA polymerase," *J. Biol. Chem.*, 279, No. 12, p. 11834-11842 (2004).

Giller et al., "Incorporation of reporter molecule-labled nucleotides by DNA polymerases. I. Chemical synthesis of various reporter group-labeled 2'deoxyribonucleoside-5'-triphosphates," *Nucleic Acids Res.*, 31, No. 10, p. 2630-2635 (2003).

Giusti, W. et al., "Synthesis and Characterization of 5'—Fluorescent-dye-labeled Oligonucleotides", *PCR Methods and Applications*, 2:223-227 (1993).

Goll et al., "Microvalves with bistable buckled polymer diaphragms," *J. Micromech. Microeng.*, vol. 6., pp. 77-79 (1996).

Goodwin, P.M., et al., "Application of single molecule detection to DNA sequencing." *Nucleosides & Nucleotides*, 16(5-6): p. 543-550 (1997).

Gravesen et al., "Microfluidics—a review", *J. Micromech. Microeng.*, vol. 3, pp. 168-182 (1993).

Greene, T.W. and P.G.M. Wuts, "Protective Groups in Organic Synthesis." John Wiley & Sons, Inc.: New York, 1999 3rd Ed.

Gueroui, Z., et al., "Observation by fluorescence microscopy of transcription on single combed DNA," *PNAS*, 99(9): p. 6005-6010 (2002).

Guilbault, G., "Practical Fluorescence—Theory, Methods and Techniques," Chapters 1 and 3, and pp. 521-524, Marcel Dekker, Inc., New York (1973).

Guillier, F., D. Orain, and M. Bradley, "Linkers and Cleavage Strategies in Solid-Phase Organic Synthesis and Combinatorial Chemistry." Chemical Reviews, 100(6): p. 2091-2157 (2000).

Gupta, K.C., et al., "A general method for the synthesis of 3'-sulfhydryl and phosphate group containing oligonucleotides", *Nucleic Acids Res.*, 1901:3019-25 (1991).

Gyllenstein, U. et al., "Generation of single-stranded DNA by the polymerase chain reaction and its application to direct sequencing of the *HLA-DQA* locus", *PNAS*, 85:7652-56 (1988).

Ha, "Single molecule dynamics studied by polarization modulation," *Phys. Rev. Lett.*, 77, No. 19, 3979-3982 1996).

Ha, "Single molecule spectroscopy with automated positioning," *Appl. Phys. Lett.* 70, No. 6, 782-784 (1997).

Ha, "Single-molecule fluorescence methods for the study of nucleic acids," Current Opinion in Struct Bio, 11, 287-292 (2001).

Ha et al., "Single-molecule fluorescence spectroscopy of enzyme conformational dynamics and cleavage mechanism," *PNAS*, 96(3): p. 893-898 (1999).

Ha, T., "Single-molecue fluorescence resonance energy transfer," *Methods*, 25(1): p. 78-86 (2001).

Hanna, M. et al., "Synthesis and characterization of a new photocrosslinking CTP analog and its use in photoaffmity labeling *E. coli* and T7 RNA polymerases", *Nucleic Acids Res.*, 21(9):2073-2079 (1993).

Hansen, C.J., et al., "A robust and scalable microfluidic metering method that allows Protein crystal growth by free interface diffusion". Proc Natl Acad Sci U S A, 99 (26): p. 16531-6 (2002).

Harding et al., "Single-molecule detection as an approach to rapid DNA sequencing," Trends in Biotechnology, vol. 10, 3 pages, (1992).

Harris, J.M., "Introduction to Biochemical and biomedical applications of poly(ethylene glycol)." Poly(ethylene glycol) Chemistry, Harris, J. M., Ed.; Plenum Press: New York, pp. 1-14 (1992).

Harrison et al., "Micromachining a miniaturized capillary electrophoresis-based chemical analysis system on a chip," Science, vol. 261, pp. 895-897 (1993).

Harrison, D., et al., "Towards miniaturized electrophoresis and chemical analysis systems on silicon: an alternative to chemical sensors", *Sensors and Actuators B*, 10, pp. 107-116 (1993).

Hasan, A. et al., "Photolabile Protecting Groups for Nucleosides: Synthesis and Photodeprotection Rates", *Tetrahedron*, 53(12):4247-4264 (1997).

Hornbeck, L. et al., "Bistable Defonnable Mirror Device", 1988 Techllical Digest Series, vol. 8, Optical Society of America, pp. 107-110, (Jun. 1988).

Hosokawa et al., "Handling of Picoliter liquid samples in a poly(dimethylsiloxane)-based microfluidic device," Anal. Chem., vol. 71, No. 20, pp. 4781-4785 (1999).

Houseal, T. et al., "Real-time imaging of single DNA molecules with fluorescence microscopy", *Biophys. 1.*, vol. 56, pp. 507-516 (Sep. 1989).

Howorka, et al., "Sequence-specific detection of individual DNA strands using engineered nanopores." Nature Biotechnology, 19(7): p. 636-639 (2001).

Hubner et al., "Direct observation of the triplet lifetime quenching of single dye molecules by molecular oxygen," J. Chem. Physics, 115, No. 21, p. 9619-9622 (2001).

Hultman, T. et al., "Bidirectional Solid-Phase Sequencing of In Vitro-Amplified Plasmid DNA", BioTechniques, vol. 10, No. 1, pp. 84-93 (1991).

Hyman, E., "A New Method of Sequencing DNA", Anal. Biochem., 174:423-436 (1988).

Ikuta et al., "Three dimensional micro integrated fluid systems (MIFS) fabricated by stereo lithography", IEEE Kyushu Institute of Technology, pp. 1-6, (1994).

Ishii et al., "Fluorescence resonance energy transfer between single fluorophores attached to a coiled-coil protein in aqueous solution," Chemical Physics, 247, 163-173 (1999).

Ishijima, A. et al., "Simultaneous Observation of Individual ATPase and Mechanical Events by a Single Myosin Molecule during Interaction with Actin", Cell, vol. 92, pp. 161-171, (Jan. 1998).

Ishikawa, M. et al., "Single-Molecule Detection by Laser-Induced Fluorescence Technique with a Position-Sensitive Photon-Counting Apparatus", Appl. Phys., vol. 33, Part 1, No. 3A, pp. 1571-1576 (1994).

Jacobs et al., "Combinatorial chemistry—applications of light-directed chemical synthesis", TIBTech, vol. 12, pp. 19-26 (Jan. 1994).

Jacobson, K. et al., "International Workshop on the application of fluorescence photobleaching techniques to problems in cell biology", Workshop Summary, Federation Proceedings, vol. 42, pp. 72-79 (1983).

Jacobson, et al., "High-speed separations on a microchip," Anal. Chem., vol. 66, No. 7, pp. 1114-1118 (1994).

Jacobson, et al., Microfluidic devices for electrokinetically driven parallel and serial mixing, Anal. Chem., vol. 71, No. 20, pp. 4455-4459 (1999).

Jett, J. et al., "High-Speed DNA Sequencing: An Approach Based Upon Fluorescence Detection of Single Molecules", J. Biomolecular Structure & Dynamics, vol. 7, No. 2, pp. 301-309, (1989).

Johnston, R. et al., "Autoradiography using storage phosphor technology", Electrophoresis, 11 :355-360 (1990).

Jongeneel, C.V., et al., "Comprehensive sampling of gene expression in human cell lines with massively parallel signature sequencing". Proc Natl Acad Sci U S A, 100(8): p. 636-639 (2003).

Joos, B. et al., "Covalent Attachment of Hybridizable Oligonucleotides to Glass Supports", Anal. Biochem. 247(1):96-101 (1997).

Kambara, H. et al., "Optimization of Parameters in a DNA Sequenator using Fluorescence Detection", Biotechnology, vol. 6, pp. 816-821 (1988).

Kartalov, Emil P., et al., "Microfluidic device reads up to four consecutive base pairs in DNA sequencing-by-synthesis", Nucleic Acids Research, vol. 32, No. 9, pp. 2873-2879 (2004).

Kartalov et al., "Single-Molecule Detection and DNA Sequencing-by-Synthesis," In Partial Fulfillment of the Requirements for the Degree of Doctor Philosophy, California Institute of technology, pp. 1-160 (2004).

Kartalov et al., "Poly-Electrolyte Surface-Chemistry Platform for Fluorescence Studies of DNA on Glass", http://www.ugcs.caltech.edu/~kartalov/PEM_6.pdf, pp. 1-7, last modified Jun. 7, 2002.

Kawai et al., "A simple method of detecting amplified DNA with immobilized probes on microtiter wells", Analytical Biochemistry, 209:63-69 (1993).

Kelso et al., "Single-cell analysis by RT-PCR reveals differential expression of multiple type 1 and 2 cytokine genes among cells within polarized CD4+ T cell populations," International Immunology, 11, No. 4, 617-621 (1999).

Kenis et al., "Microfabrication inside capillaries using multiphase laminar flow patterning," Science, vol. 285, pp. 83-85 (1999).

Kenney, et al., "Mutation Typing Using Electrophoresis and Gel-Immobilized Acrydite™ Probes," BioTechniques, vol. 25, No. 3, pp. 516-521, (1998).

Khandjian, E., "UV cross linking of RNA to nylon membrane enhances hybridization signals", Mole. Bio. Rep. 11: 107-115 (1986).

Khrapko, K. et al., "A method for DNA sequencing by hybridization with oligonucleotide matrix", DNA Sequence-J. DNA Sequencing and Mapping, vol. 1, pp. 375-388 (1991).

Kiefer, J. et al., "Crystal structure of a thermostable Bacillus DNA polymerase 1 large fragment at 2.1 A resolution", Structure, 5:95-108 (1997).

Kim, Y. et al., "Crystal structure of Thermus aquaticus DNA polymerase", Nature, 376:612-616 (1995).

Kirkland, T.A., D.M. Lynn, and R.H. Grubbs, "Ring-Closing Metathesis in Methanol and Water." Journal of Organic Chemistry, 63(26): p. 9904-9909 (1998).

Knerr, L. and R.R. Schmidt, "Application of a ring-closing-metathesis-based linker to the solid phase synthesis of oligosaccharides" Synlett, 11: p. 1802-1804 (1999).

Kopp, et al., "Chemical Amplification: Continuous-Flow PCR on a Chip", Science, vol. 280, pp. 1046-1048 (May 1998).

Korolev, S. et al., "Crystal structure of the large fragment of Thermus aquaticus DNA polymerase I at 2.5 A resolution: Structural basis for thermo stability", PNAS, 92:9264-9268 (1995).

Kovacs et al., "Simple synthesis of 5-vinyl-and 5-ethynyl-2' deoxyuridine 5'-triphosphates", Tetrahedron Letters, 29(36): p. 4525-8 (1988).

Kricka et al., "Labels, Labeling, Analytical Strategies, and Applications." Ch. 1 and Table Ix, Academic Press, New York, pp. 3-40, (1995).

Krider, E. et al., "2'-Modified Nucleosides for Site-Specific Labeling of Oligonucleotides", Bioconjugate Chem., vol. 13, No. 1, pp. 155-162 (2002).

Kuhn, L. et al., "Silicon Charge Electrode Array for Ink Jet Printing", IEEE Trans. On Electron Dev., vol. ED-25, No. 10, pp. 1257-1260 (Oct. 1978).

Lacoste, T. et al., "Ultrahigh-resolution multicolor colocalization of single fluorescent probes", PNAS, 97(17):9461-6 (2000).

Lander, E.S., et al., "Initial sequencing and analysis of the human genome." Nature, 409(6822): p. 860-921 (2001).

Lazowski, K. et al., "Highly Sensitive Detection of Hybridization of Oligonucleotides to Specific Sequences of Nucleic Acids by Application of Fluorescence Resonance Energy Transfer", Antisense and Nucleic Acid Drug Dev., vol. 10, pp. 97-103 (2000).

Lee, "Enhancing the catalytic repertoire of nucleic acids: a systematic study of linker length and rigidity," Nucleic Acids Res., 29, No. 7, Apr. 1, 1565-1573 (2001).

Lee, Y. et al., "Laser-Induced Fluorescence Detection of a Single Molecule in a Capillary", Anal. Chem., vol. 66, pp. 4142-4149 (1994).

Levene, M. et al., "Zero-Mode Waveguides for Single-Molecule Analysis at High Concentrations", Science, 299:682-686 (Jan. 2003).

Levsky et al., "Single-cell gene expression profiling," Science, 297, 836-840 (2002).

Li, H. et al., "Ultrasensitive Coincidence Fluorescence Detection of Single DNA Molecules", Anal. Chem., 75:1664-1670 (2003).

Li, Y. et al., "Design, Synthesis, and Spectroscopic Properties of Peptide-Bridged Fluorescence Energy-Transfer Cassettes", Bioconjuate Chem., 10:241-245 (1999).

Li, Y. et al., "Structural Studies of the Klentaql DNA Polymerase", Current Organic Chem., 5:871-883 (2001).

Li, Z. et al., "A photocleavable fluorescent nucleotide for DNA sequencing and analysis", PNAS, vol. 100, No. 2, pp. 414-419 (2003).

Lin, L. et al., "Free-Space Micromachined Optical Switches for Optical Networking", IEEE J. of Selected Topics in Quanturn Electronics, vol. 5, No. 1, pp. 4-9 (Jan. 1999).

Liu, J., M.. Enzelberger, and S. Quake, "A nanoliter rotary device for polymerase chain reaction" Electrophoresis, 23(10): p. 1531-6 (2002).

Lodder, M., et al., "Misacylated Transfer RNAs Having a Chemically Removable Protecting Group." Journal of Organic Chemistry, 63(3): p. 794-803 (1998).

Loh, E. et al., "Polymerase Chain Reaction with Single-Sided Specificity: Analysis of T Cell Receptor D Chain", Science 243:217-220 (1989).

Lok, Corie, "Deciphering DNA, Top Speed—Helicos BioSciences aims to expedite sequencing, enable genomic medicine," Technology Review, pp. 27-28 (May 2005).

Lopez, G. et al., "Fabrication and Imaging of Two-Dimensional Patterns of Proteins Adsorbed on Self-Assembled Monolayers by Scanning Electron Microscopy", *J. Arner. Chem. Soc.*, 115:10774-81 (1993).

Lotters et al., "The mechanical properties of the rubber elastic polymer polyimethylsiloxane for sensor applications," J. Micromech. Microeng., vol. 7, pp. 145-147 (1997).

Lucy et al., "Characterization of the cationic surfactant induced reversal of electroosmotic flow in capillary electrophoresis," Anal. Chem., vol. 68, pp. 300-305 (1996).

Ludwig, J and F. Eckstein, "Rapid and Efficient Synthesis of Nucleoside 5'-$O$-(1-Thiotriphosphates), 5'-triphosphates and 2',3'-Cyclophosphorothioates Using 2-Chloro-4$H$-1,3,2-benzodioxaphosphorin-4-one." Journal of Organic Chemistry, 54(3): p. 631-635 (1989).

Lvov, Yu. et al., "Assembly of Thin Films by Means of Successive Deposition of Alternate Layers of DNA and Poly(allylamine)", *American Chemical Society, Macromolecules*, 26, pp. 5396-5399, (1993).

Macklin, J. et al., "Imaging and Time-Resolved Spectroscopy of Single Molecules at an Interface", *Science*, vol. 272, No. 5259, pp. 255-258 (Apr. 1996).

Maier, B., D. Bensimon, and V. Croquette, "Replication by a single DNA polymerase of a stretched single-stranded DNA." Proceedings of the National Academy of Sciences of the United States of America, 97(22): p. 12002-12007 (2000).

Marriott, G. et al., "Time resolved imaging microscopy—Phosphorescence and delayed fluorescence imaging", *Biophys. J.*, vol. 60, pp. 1374-1387 (Dec. 1991).

Marziali, A. and M. Akeson, "New DNA sequencing methods." Annual Review of Biomedical Engineering, 3: p. 195-223 (2001).

Mastrangelo, C. et al., "Vacuum-Sealed Silicon Micromachined Incandescent Light Source", *IDEM*, 89:503-506 (1989).

Meiners, J.C and S.R. Quake, "Femonewton force spectroscopy of single extended DNA molecules." Phys Rev Lett, 84(21): p. 5014-7 (2000).

Meldrum, Kevin, "Microfluidics-based products for nucleic acid analysis", http://www.americanlaboratory.com/articles/al/a9909mel.pdf, 2 pages (Sep. 1999).

Meller, A., et al., "Rapid nanopore discrimination between single polynucleotide molecules." *PNAS*, 97(3): p. 1079-1084 (2000).

Mertz, J. et al., "Single-molecule detection by two-photon-excited fluorescence", *Optics Letters*, vol. 20, No. 24, pp. 2532-2534 (Dec. 1995).

Metzker et al., "Elimination of residual natural nucleotides from 3'-O-modified-dNTP syntheses by enzymatic mop-up," BioTechniques, 25, 814-817 (1998).

Metzker, M.L., et al., "Termination of DNA synthesis by novel 3'-modified-deoxyribonucleoside 5'-triphosphates." Nucleic Acids Res, 22(20): p. 4259-67 (1994).

Mitra, Robi, et al., "Fluorescent in situ sequencing on polymerase colonies", *Analytical Biochemistry*, 320, pp. 55-65 (2003).

Moe et al., Rapid Detection of Clinically Relevant Bacteria in Platelets Using the Hybriscan Baceterial Detection system, Journal of the American Society of Hematology, 96, No. 11, 4155 (2000).

Moore, P., "To affinity and beyond", *Nature*, vol. 426, No. 6967, pp. 725-731, (2003).

Muller et al., "Surface-micromachined microoptical elements and systems," IEEE vol. 86, No. 8, pp. 1705-1720 (1998).

Nelson, P. et al., "Bifunctional oligonucleotide probes synthesized using a novel CPG support are able to detect single base pair mutations", *NAR*, 17(18):7187-7194 (1989).

Nie, S. et al., "Probing Individual Molecules with Confocal Fluorescence Microscopy", *Science*, vol. 266, No. 5187, pp. 1018-1021 (Nov. 1994).

Nyren, P. et al., "Solid Phase DNA Minisequencing by an Enzymatic Luminometric Inorganic Pyrophosphate Detection Assay", *Anal. Biochem.*, vol. 208, pp. 171-175 (1993).

Ochman, H. et al., "Genetic Applications of an Inverse Polymerase Chain Reaction", *Genetics* 120:621-623 (1988).

Ohara, To et al, "'Wired' Enzyme Electrodes for Amperometric Determination of Glucose or Lactate in the Presence of Interfering Substances",Ana/. Chem., vol. 66, No. 15, pp. 2451-2457 (Aug. 1994).

Ohara, T. et al., "Glucose Electrodes Based on Cross-Linked [Os(bpY)2CltH Complexed Poly(1-vinylimidazole) Films", *Anal. Chem.*, vol. 65, pp. 3512-3517 (1993).

Okabe, S. et al., "Do Photobleached Fluorescent Microtubles Move?: Re-evaluation of Fluorescence Laser Photobleaching both In Vitro and in Growing *Xenopus* Axon", *J. Cell Bio.*, vol. 120, No. 5, pp. 1177-1186 (1993).

Ollis, D. et al., Structure of large fragment of *E. coli* DNA polymerase I complexed with Dtmp, *Nature*, 313:762-766 (1985).

Oroskar, A. et al., "Detection of immobilized amplicons by ELISA-like techniques" *Clin. Chem.*, 42(9):1547-1555 (1996).

Patchornik, A. et al., "Photosensitive Protecting Groups" *J. Arner. Chem. Soc.*, 92(21):6333-37 (1970).

Padmaja, T., et al., "Enzymatically degradable prodrugs: a novel methodology for drug linkage." Journal of Applied Polymer Science, 85(10): p. 2108-2118 (2002).

Pennisi, E., "Gene researchers hunt bargins, fixer-uppers." Science, 298(5594): p. 735-736 (2002).

Perales et al., "Enhancement of DNA, cDNA synthesis and fidelity at high temperatures by a dimeric single-stranded DNA-binding protein," Nucleic Acids Res., 31, No. 22, 6473-6480 (2003).

Perkins, T. et al., "Relaxation of a Single DNA Molecule Observed by Optical Microscopy", *Science*, 264:822-826 (May 1994).

Pethig, R. et al, "Applications of dielectrophoresis in biotechnology", *Tibtech*, vol. 15, pp. 426-432 (Oct. 1997).

Pisani, F. et al, "Domain Organization and DNA-Induced Conformational Changes of an Archaeal Family B DNA Polymerase", *Biochemistry*, vol. 35, pp. 9158-9166 (Jul. 1996).

Plakhotnik, T. et al, "Single-Molecule Spectroscopy", *Annu. Rev. Phys. Chem.*, vol. 48, pp. 181-212 (1997).

Ploem, J., Ch. 1 "Fluorescence Microscopy", Fluorescent and Luminescent Probes for Biological Activity, Mason, T. Ed., Academic Press, London, pp. 1-11 (1993).

Qin et al., "Elastomeric Light Valves," *Advanced Materials*, vol. 9, No. 5, pp. 407-410 (1997).

Qin, P. et al., "Site-Specific Labeling of RNA with Fluorophores and Other Structural Probes", *Methods*, vol. 18, No. 1, pp. 60-70 (May 1999).

Quake, S. et al., "Fluorescent Photobleaching Method for Sequencing DNA", pp. 1-10, circa 1996.

Quake, Stephen R. et al., "Methods and Apparatuses For Analyzing Polynucleotide Sequences", pending U.S. patent application, U.S. Appl. No. 09/707,737, filed Nov. 6, 2000.

Quake, S. et al., "Polymer Physics with Single Molecules of DNA" (Dept. of Physics), a colloquium by Stephen Quake, Stanford University, Feb. 22, 1996. (Presented at Laser Spectroscopy XII Intl. Conference, Italy, Jun. 1995).

Quake, S. et al., "From Micro- to Nanofabrication with Soft Materials", *Science*, vol. 290, No. 5496, pp. 1536-1540 (Nov. 2000).

Rapp, R. et al., "LIGA micropump for gases and liquids", *Sensors and Actuators A*, vol. 40, pp. 57-61 (1994).

Rasolonjatovo I. and S.R. Sarfati, "6-N-(N-methylanthranyamido)-4-oxo-hexanoic acid: a new florescent protecting group applicable to a new DNA sequencing method." Nucleosides & Nucleotides, 17(9-11): p. 2021-2025 (1998).

Rasolonjatovo, I. and Sarfati, "Development of a new DNA sequencing method: 3'-ester cleavage catalyzed by Taq DNA polymerase." Nucleosides & Nucleotides, 18(4 & 5): p. 1021-1022 (1999).

Reha-Krantz, L. et al., "Genetic and Biochemical Studies of Bacteriophage T4 DNA Polymerase 3'→5'-Exonuclease Activity", *The Journal of Biological Chemistry*, vol. 268, No. 36, pp. 27100-27108 (1993).

Reha-Krantz, L. et al., "Motif A of Bacteriophage T4 DNA Polymerase: Role in Primer Extension and DNA Replication Fidelity", *The Journal of Biological Chemistry*, vol. 269, No. 8, pp. 5635-5643 (1994).

Rigler, R, et al, "DNA-sequencing at the single molecule level." Journal of Biotechnology, 86(3): p. 161 (2001).

Rigler, R., "Fluorescence correlations, single molecule detection and large number screening—Applications in Biotechnology", *J. Biotech.*, 41: 177-186 (1995).

Ronaghi, M. et al., "A Sequencing Method Based on Real-Time Pyrophosphate", *Science*, vol. 281, pp. 363-365 (Jul. 1998).

Ronaghi, M et al., "Real-Time DNA Sequencing Using Detection of Pyrophosphate Release." *Analytical BioChemistry*, 242, No. 0432, (1996).

Rosenblum, B. et al., "New dye-labled terminators for improved DNA sequencing patterns",*Nucleic Acids Research*, vol. 25, No. 22, pp. 4500-4504 (Nov. 1997).

Rosenblum, B. et al., "Improved single-strand DNA sizing accuracy in capillary electrophoresis", *Nucleic Acids Research*, vol. 25, No. 19, pp. 3925-3929 (Oct. 1997).

Roylance, L. et al., "A Batch-Fabricated Silicon Accelerometer", *IEEE Trans. On Elec. Dev.*, vol. ED-26, No. 12, pp. 1911-1917 (1979).

Ruparel, Hameer, "Design and synthesis of a 3'-O-allyl photocleavable fluorescent nucleotide as a reversible terminator for DNA sequencing by synthesis", *PNAS*, vol. 102, No. 17, pp. 5932-5937 (Apr. 26, 2005).

Ruth, J. et al., "Nucleoside Analogues with Clinical Potential in Antivirus Chemotherapy", *Molecular Pharmacology*, 20:415-422 (1981).

Sanger, F. et al., "DNA sequencing with chain-terminating inhibitors", *PNAS*, 74(12):5463-67 (Dec. 1977).

Sarfati, S.R., et al., "Synthesis of fluorescent derivatives of 3'-O-(6-aminohexanoyl)-pyrimidine nucleosides 5'-triphosphates that act as DNA polymerase substrates reversibly tagged at C-3'." Journal of the Chemical Society, Perkin Transactions 1: Organic and Bio-Organic Chemistry, 9: p. 1163-71 (1995).

Sato, E. et al., "Bimane Conjugates of 5-Halogenouridylic Acids as Fluorogenic Substrates for Phosphodiesterase I", *J. Chem. Research (S)*, Issue 10, pp. 390-391 (1994).

Satoh, Ikuo et al., "Flow-injection determination of inorganic pyrophosphate with use of an enzyme thermistor containing immobilized inorganic pyrophosphatase", *Chemical Abstracts*, vol. 110, No. 16, pp. 409-413 (1988).

Sauer, M., et al.., "Single molecule DNA sequencing in submicrometer channels: state of the art and future prospects." Journal of Biotechnology, 86(3): p. 181-201 (2001).

Schasfoort et al., "Field-effect flow control for microfabricated fluidic networks," Science, vol. 286, pp. 942-945 (1999).

Schueller, O., et al., "Reconfigurable diffraction gratings based on elastomeric microfluidic devices", *Sensors and Actuators*, 78, pp. 149-159 (1998).

Seeger, S. et al., "Single molecule fluorescence—High Performance Molecular Diagnosis and Screening", translated from *BIOforum*, pp. 179-185, (Apr. 1998).

Selvin, P., "Fluorescence Resonance Energy Transfer", *Meth. In Enzymology*, vol. 246, pp. 300-335, Academic Press (1995).

Seo, Tae Seok, "Four-color DNA sequencing by synthesis on a chip using photocleavable fluorescent nucleotides", *PNAS*, vol. 102, No. 17, pp. 5926-5931 (Apr. 26, 2005).

Seo, Tae Seok, "Photocleavable fluorescent nucleotides for DNA sequencing on a chip constructed by site-specific coupling chemistry", *PNAS*, vol. 101, No. 15, pp. 5488-5493 (Apr. 13, 2004).

Shackelford, James F., "Intro. to Materials Science for Engineers," 3rd Edition, Prentice-Hall, Inc., Macmillan Publ. Co. (1992) (cited by Examiner E. Quan in related case).

Shendure et al., "Advanced sequencing technologies: Methods and goals," Nature Reviews, vol. 5, No. 5, pp. 335-344 (2004).

Shoji, S. et al., "Smallest Dead Volume Microvalves for Integrated Chemical Analyzing Systems", *Proceedings of Transducers '91*, IEEE, pp. 1052-1055, San Francisco (1991).

Shoji, S. et al., "Fluids for Sensor Systems." Microsystem Technology in Chemistry and Life Science, Topics in Current Chem., vol. 194, pp. 162-188, Springer-Verlag (1998).

Smith, L. et al., "Fluorescence detection in automated DNA sequence analysis", *Nature*, vol. 321, pp. 674-679 (Jun. 1986).

Smith, L. et al., "The synthesis of oligonucleotides containing an aliphatic amino group at the 5' terminus: synthesis of fluorescent DNA primers for use in DNA sequence analysis", *Nucleic Acids Res.*, vol. 13, No. 7, pp. 2399-2412 (1985).

Smith, S. et al., "Direct Mechanical Measurements of the Elasticity of Single DNA Molecules by Using Magnetic Beads", *Science* 258:1122-26 (1992).

Smits, I., "Piezoelectric Micropump with Three Valves Working Peristaltically", *Sensors and Actuators*, vol. A21-A23, pp. 203-6 (1990).

Song et al., "Influence of the triplet excited state on the photobleaching kinetics of fluorescein in microscopy," Biophysics J., 70, 2959-2968 (1996).

Sproat, B. et al., "The synthesis of protected 5'-mercapto-2',5'-dideoxyribonucleoside-3'-O-phosphoramidities; uses of 5'-mercapto-oligodeosyribonucleotides", *Nucleic Acids Res.*, 15(12):4837-48 (1987).

Stocki, S. et al., "Dynamics of Bacteriophage T4 DNA Polymerase Function: Identification of Amino Acid Residues that Affect Switching between Polymerase and 3'→5'-Exonuclease Activities", *J. Mol. Biol.*, 254, pp. 15-28 (1995).

Strausberg, R L, et al., "The mammalian gene collection." Science, 286(5439): p. 455-7 (1999).

Sukhorukov, G.B., et al., "Assembly of polyelectrolyte multilayer films by consecutively alternating adsorption of polynucleotides and polycations", *Thin Solid Films*, 284-285, p. 220-223 (1996).

Tasara et al., "Incorporation of reporter molecule-labeled nucleotides by DNA polymerases. II. High-density labeling of natural DNA," Nucleic Acids Res., 31, No. 10, 2636-2646 (2003).

Taveira, N. et al., "Detection of HI VI proviral DNA by PCR and hybridization with digoxigenin labeled probes", *Mol. Cell Probes*, vol. 6, No. 4, pp. 265-270 (1992).

Taylor, D. et al., "Characterization of chemisorbed monolayers by surface potential measurements", J. *Phys. D. Appl. Phys.* 24:1443-50 (1991).

Terry, S. et al., "A Gas Chromatographic Air Analyzer Fabricated on a Silicon Wafer", *IEEE Trans. on Electron Dev.*, vol. ED-26, No. 12, pp. 1880-1886 (1979).

Theisen, P. et al., "Fluorescent dye phosphoramidite labeling of oligonucleotides", *Nucleic Acids Symp. Ser.*, vol. 27, pp. 99-100 (1992).

Thompson, N. et al., "Measuring Surface Dynamics of Biomolecules by Total Internal Reflection Fluorescence with Photobleaching Recovery or Correlation Spectroscopy", *Biophys. J.*, vol. 33, pp. 435-454 (Mar. 1981).

Thompson, N. et al., "Immunoglobulin Surface-Binding Kinetics Studied by Total Internal Reflection with Fluorescence Correlation Spectroscopy", *Biophys. J.*, vol. 43, pp. 103-114 (Jul. 1983).

Thorsen, T. S.J. Maerkl, and S.R. Quake, "Microfluidic large-scale integration." Science, 298(5593): p. 580-4 (2002).

Tokunaga, M. et al., "Single Molecule Imaging of Fluorophores and Enzymatic Reactions Achieved by Objective-Type Total Internal Reflection Fluorescence Microscopy", *Biochem. And Biophys. Res. Comm.*, vol. 235, pp. 47-53 (1997).

Toneguzzo, F. et al., "Use of a Chemically Modified T7 DNA Polymerase for Manual and Automated Sequencing of Super coiled DNA", *BioTech*, vol. 6, No. 5, pp. 460-9 (1988).

Trager, R. S., "DNA sequencing—Venter's next goal: 1000 human genomes." Science, 298(5595): p. 947 (2002).

Tufte, O. et al., "Silicon Diffused-Element Piezoresistive Diaphragms", *J. Applied Phys.*, vol. 31, No. 11, pp. 3322-3327 (Nov. 1962).

Tyagi, S. et al., "Multicolor molecular beacons for allele discrimination", *Nat. Biotechnol.*, 16:49-53 (1998).

Ullman's Encyclopedia of industrial Chemistry, 61D Edition, vol. 6, Sections 6 to 6.3, Subject: Carbon Black, Wiley-VCH (1999).

Unger et al., "Monolithic microfabricated valves and pumps by multilayer soft lithography," Science 288: 113-116 (2000).

Unger, M. et al., "Single-Molecule Fluorescence Observed with Mercury Lamp Illumination", *BioTechniques*, vol. 27, PD. 1008-1014 (Nov. 1999).

Vale, R. et al., "Direct observation of single kinesin molecules moving along microtubules", *Nature*, vol. 380, pp. 451-3, (Apr. 1996).

Van Dam, R.M. and S.R Quake, "Gene expression analysis with universal n-mer arrays." Genome Res, 12(1): p. 145-52 (2002).

Van De Pol, F. et al., "Micro-liquid handling devices: A Review", Micro System Technologies 90, 1st Intl. Conf. On Micro Electro, Opto, Mechanic Systems and Components, pp. 799-805, Berlin, Springer-Verlag, (1990).

Van Oijen et al., "Single molecule kinetics of λ exonuclease reveal base dependence and dynamic disorder," Science, 301, 1235-1238 (2003).

Venter, J.L., et al., "The sequence of the human genome." Science, 291(5507): p. 1304-1351 (2001).

Vieider, C. et al., "A Pneumatically Actuated Micro Valve With A Silicone Rubber Membrane For Integration With Fluid-Handling Systems", *Proceedings of Transducers '95*, pp. 284-286, Stockholm (1995).

Walker, M.G., et al., "Prediction of gene function by genome-scale expression analysis: Prostate cancer-associated genes.": Genome Researce, 9(12): p. 1198-1203 (1999).

Wang, G. et al., "Design and Synthesis of New Fluorogenic HIV Protease Substrates Based on Resonance Energy Transfer", *Tetrahedron Lett.*, 31(45):6493-96 (1990).

Wang, M.D., et al., "Force and Velocity measured for single molecules of RNA polymerase." Science, 282(5390): p. 902-907 (1998).

Washizu et al., "Molecular dielectrophoresis of biopolymers," IEEE Transactions on Industry Applications, vol. 30, No. 4, pp. 835-843 (1994).

Watkins, R. et al., "A Total Internal-Reflection Technique for the Examination of Protein Adsorption", *J. Biomed. Mater. Res.*, vol. 11, pp. 915-938 (1977).

Weber, J.L. and E.W. Myers, "Human whole-genome shotgun sequencing." Genome Research, 7(5): p. 401-409 (1997).

Webster, J. et al., "Monolithic Capillary Gel Electrophoresis Stage with On-Chip Detector", Intl. Conf. on MEMS (MEMS 96), pp. 491-496 (1996).

Wedekind, P. et al., "Scanning microphotolysis: a new photobleaching technique based on fast intensity modulation of a scanned laser beam and confocal imaging", *J. Microscopy*, vol. 176, Pt. 1, pp. 23-33 (Oct. 1994).

Weir, et al., "Hybrigel Purification: A Novel Technique for Accelerated Prepration of DNA Sequence Products for Capillary Electrophoresis and Multiplexing," Clinical Chemistry, vol. 45, No. 11, p. 2052 (1999).

Weiss, S., "Fluorescence Spectroscopy of Single Biomolecules", *Science*, vol. 283, pp. 1676-1683 (Mar. 1999).

Welch, M.B. and K. Burgess, "Synthesis of fluorescent, photolabile 3'-O-protected nucleoside triphosphates for the base addition sequencing scheme." Nucleosides & Nucleotides, 18(2): p. 197-201 (1999).

Werner et al "Progress towards single-molecule DNA sequencing: a one color demonstration." J Biotechnol, 102(1): p. 1-14 (2003).

Williams, N. et al., "Exploring the Adenine Nucleotide Binding Sites on Mitochondrial $F_1$-ATPase with a New Photoaffinity Probe, 3'-O-(4-Benzoyl)benzoyl Adenosine 5'-Triphosphate", *J. Bioi. Chem.*, 237(6):2834-41 (1982).

Winter et al., "Direct gene expression analysis," Curr. Pharm. Biotech., 5, p. 191-1997 (2004).

Wu, et al., "Synthesis and Properties of Adenosine-5'-triphosphoro-γ-1-(5-sulfonic acid)naphthyl Ethylamide: A Fluorescent Nucleotide Substrate for DNA-Dependent RNA Polymerase from *Escherichia coli*," Archives of Biochemistry and Biophysics, vol. 246, No. 2, pp. 564-571 (1986).

Wuite, G. et al., "Single-molecule studies of the effect of template tension on T7 DNA polymerase activity", *Nature*, 404:103-6 (2000).

Xia et al., "Complex optical surfaces formed by replica molding against elastomeric masters," Science vol. 273, pp. 347-349 (1996).

Xia et al. "Soft Lithography," Angew. Chem. Int. Ed. vol. 37, pp. 550-575 (1998).

Xia, G., et al., "Directed evolution of novel polymerase activities: mutation of a DNA polymerase into a efficient RNA polymerase." Proc Natl Acad Sci USA; 99(10) p. 6597-6602 (2002).

Xie, "Single molecule approach to dispersed kinetics and dynamic disorder: Probing conformational fluctuation and enzymatic dynamics," J. Chem. Physics, 117, No. 24, p. 11024-11032 (2002).

Xu, X. et al., "Direct Measurement of Single-Molecule Diffusion and Photodecomposition in Free Solution", *Science*, vol. 275, pp. 1106-1109, (Feb. 1997).

Xu, X. et al., "Long-Range Electrostatic Trapping of Single-Protein Molecules at a Liquid-Solid Interface", *Science*, vol. 281, pp. 1650-1653 (Sep. 1998).

Yang et al., "A Mems Thermopneumatic Silicone Rubber Membrane Valve", Proceedings of IEEE 10th Annual International Workshop on MicroElectro Mechanical Systems, Sensors and Actuators, vol. A64, No. 1, pp. 101-8 (1998).

Yazdi, N. et al., "Micromachined Intertial Sensors", *Proceedings of the IEEE*, vol. 86, No., pp. 1640-1659 (Aug. 1998).

Yershov, G. et al., "DNA analysis and diagnostics on oligonucleotide microchips", *Proc. Natl. Acad. Sci. USA*, vol. 93, pp. 4913-4918 (May 1996).

Young et al., "Contoured elastic-membrane microvalves for microfluidic network integration," J. Biomechanical Engineering, vol. 121, pp. 2-6 (1999).

Yu., et al., "Cyanine dye dUTP analogs for enzymatic labeling of DNA probes." Nucleic Acids Res, 22(15): p. 3226-32 (1994).

Zdeblick, M. et al., "A Microminiature Electric-To-Fluidic Valve", Transducers '87, reprinted in *Micromechanics and MEMS Classic and Seminal Papers to 1990*, IEEE Press, pp. 437-439 (1987).

Zhu, Z. et al., "Molecular Mechanism Controlling the Incorporation of Fluorescent Nucleotides into DNA by PCR", *Cytometry*, 28:206-211 (1997).

Zhu, Z. et al., "Directly labeled DNA probes using fluorescent nucleotides with different length linkers", *Nucleic Acids Res.*, vol. 22, No. 16, pp. 3418-3422 (1994).

Zuckerman, R. et al., "Efficient methods for attachment of thiol specific probes to the 3' ends of synthetic oilgodeoxyribonucleotides", *Nucleic Acids Res.*, 15(13):5305-5321 (1987).

Therminator DNA Polymerase FAQ, http://www.neb.com/nebecomm/products/faqproductM0261.asp downloaded Jun. 1, 2005, 1 page.

\* cited by examiner

METHODS AND COMPOSITIONS FOR IMPROVING FIDELITY IN A NUCLEIC ACID SYNTHESIS REACTION

TECHNICAL FIELD OF THE INVENTION

The invention generally relates to methods for improving fidelity in a nucleic acid synthesis reaction, and more particularly to methods for sequencing a nucleic acid using a nucleotide derivative that decreases the rate of misincorporation of nucleotides in a nucleic acid synthesis reaction.

BACKGROUND OF THE INVENTION

Figure 1:
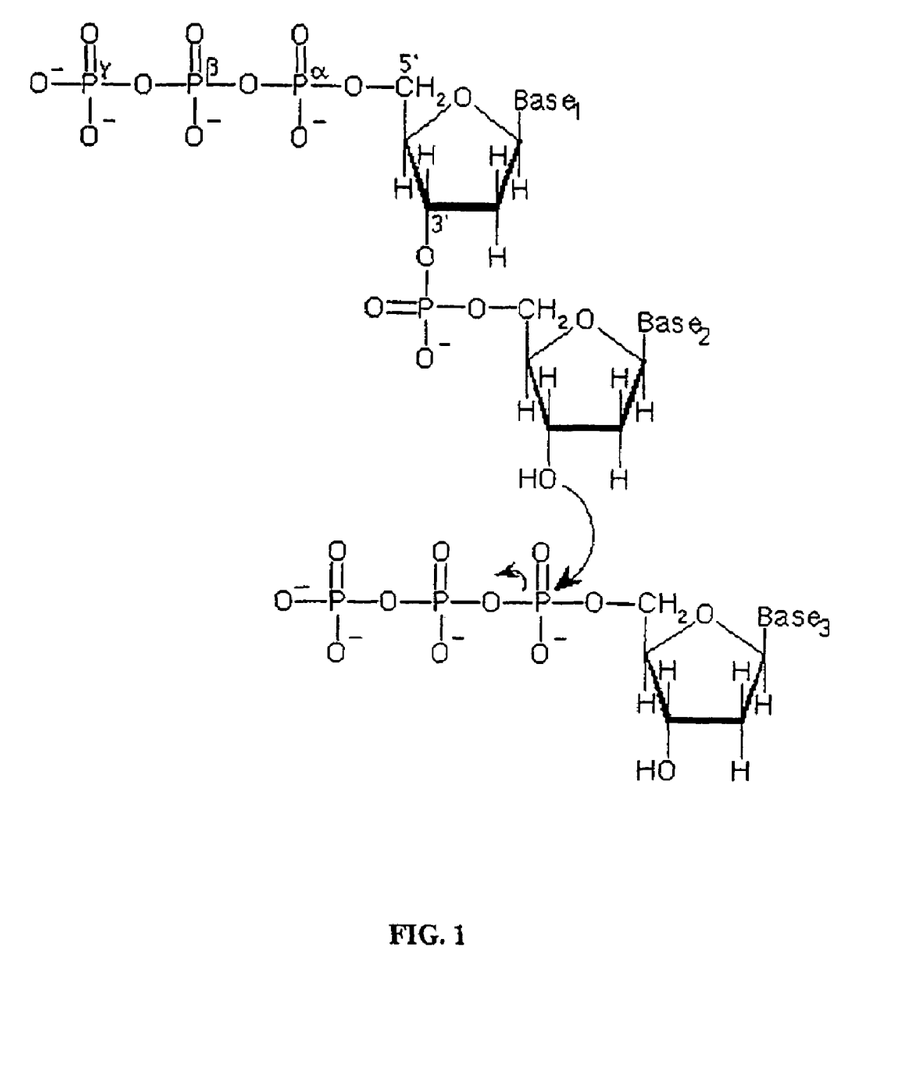
FIG. 1 is a schematic representation of a polymerization reaction that results in the addition of a nucleotide to a polynucleotide.

In vitro nucleic acid synthesis is a foundation of many fundamental research and diagnostic tools, such as nucleic acid amplification and sequencing. In a template-dependent nucleic acid synthesis reaction, the sequential addition of nucleotides is catalyzed by a nucleic acid polymerase. Depending on the template and the nature of the reaction, the nucleic acid polymerase may be a DNA polymerase, an RNA polymerase, or a reverse transcriptase. DNA synthesis requires a 3' hydroxyl on the primer for addition at the α-phosphate of a free deoxynucleotide triphosphate (dNTP). A phosphodiester bond between the nucleotide on the 3' terminus of the primer and the free nucleotide is formed and diphosphate is released. This reaction is shown schematically in FIG. 1.

The fidelity of template-dependent nucleic acid synthesis depends in part on the ability of the polymerase to discriminate between complementary and non-complementary nucleotides. Normally, the conformation of the polymerase enzyme favors incorporation of the complementary nucleotide. However, there is still an identifiable rate of misincorporation that depends upon factors such as local sequence and the base to be incorporated.

Synthetic or modified nucleotides and analogs, such as labeled nucleotides, tend to be incorporated into a primer less efficiently than naturally-occurring dNTPs. The reduced efficiency with which the unconventional nucleotides are incorporated by the polymerase can adversely affect the performance of sequencing techniques that depend upon faithful incorporation of such unconventional nucleotides.

Single molecule sequencing techniques allow the evaluation of individual nucleic acid molecules in order to identify changes and/or differences affecting genomic function. In single molecule techniques, individual, optically-resolvable nucleic acid fragments are attached to a solid support, and sequencing is conducted on the individual strands. Sequencing events are detected and correlated to the individual strands. See Braslavsky et al., Proc. Natl. Acad. Sci., 100: 3960-64 (2003), incorporated by reference herein. Because single molecule techniques do not rely on ensemble averaging as do bulk techniques, errors due to misincorporation can have a significant deleterious effect on the sequencing results. The incorporation of a nucleotide that is incorrectly paired, under standard Watson and Crick base-pairing, with a corresponding template nucleotide during primer extension may result in sequencing errors. The presence of misincorporated nucleotides may also result in prematurely terminated strand synthesis, reducing the number of template strands for future rounds of synthesis, and thus reducing the efficiency of sequencing.

There is, therefore, a need in the art for improved methods for reducing the frequency of misincorporation and improving fidelity in nucleic acid synthesis reactions, especially in single molecule sequencing.

SUMMARY OF THE INVENTION

The invention addresses the problem of misincorporations in nucleic acid synthesis reactions. The invention improves the fidelity of nucleic acid synthesis reactions by selectively blocking incorporation of non-complementary nucleotides in a template-dependent sequencing-by-synthesis reaction. In order to block misincorporation, nucleotide derivatives that hydrogen bond to their complement on the template, but do not engage in phosphodiester bonding with adjacent primer nucleotides, are added to the reaction along with labeled standard nucleotides for incorporation into the primer. A standard (labeled) nucleotide typically will out-compete derivatives for complementary binding. In cases in which a derivative attaches at an incorporation site intended for the complementary standard nucleotide, the derivative will be washed out and the position will be occupied by a standard nucleotide in a subsequent round. Because a complementary derivative will typically out-compete a mismatched standard nucleotide for incorporation, the derivatives end up blocking misincorporation. Derivatives, which are only hydrogen-bonded to their complement, are labile in comparison to standard nucleotides, which engage in phosphodiester bonding to adjacent primer nucleotides (in addition to complement hydrogen bonding). Thus derivatives can be washed out, making their complement available for binding in subsequent nucleotide addition cycle.

Methods of the invention prevent some or all of the misincorporation errors that result in erroneous base calling and/or chain termination in sequencing reactions. According to the invention, a polymerization reaction is conducted on a nucleic acid duplex that comprises a primer hybridized to a template nucleic acid. The reaction is conducted in the presence of a polymerase, at least one free dNTP corresponding to a first nucleotide species, and at least one nucleotide derivative corresponding to a nucleotide species different from the dNTP. The nucleotide derivative comprises a modification that inhibits the formation of a phosphodiester bond between the derivative and the free 3' hydroxyl group of the terminal nucleotide on the primer. As such, the nucleotide derivative cannot incorporate into the primer. However, if the template comprises a nucleotide at a position immediately adjacent to the 3' terminus of the primer that is complementary to the nucleotide derivative, the nucleotide derivative forms hydrogen bonds with its complementary nucleotide and prevents the incorporation of the free nucleotide into the primer. According to the invention, derivatives that are complementary to an available template nucleotide out-compete misincorporating dNTPs for template binding.

In a single molecule sequencing-by-synthesis reaction, primer/template duplexes are bound to a solid support such that each duplex is individually optically detectable. According to the invention, a primer/template duplex is exposed to a polymerase, a labeled nucleotide corresponding to at least a first nucleotide species, and at least one nucleotide derivative corresponding to a nucleotide species different than the labeled species. The duplex may be simultaneously exposed to the polymerase, labeled nucleotide and nucleotide derivative; or it may be first exposed to the nucleotide derivative and then to the polymerase and labeled nucleotide. In a preferred aspect, the duplex is simultaneously exposed to the polymerase, the free nucleotide and three nucleotide derivatives, one corresponding to each of the three remaining nucleotide species. Unincorporated labeled nucleotides are washed away, and because hydrogen bonds are relatively weak, the nucleotide derivatives are removed along with the unincorporated labeled nucleotides. The incorporation of the labeled nucleotide is determined, as well the identity of the nucleotide that is complementary to a nucleotide on the template at a position that is opposite the incorporated nucleotide. The polymerization reaction is serially repeated in the presence of labeled nucleotide that corresponds to each of the other nucleotide species, and appropriate nucleotide derivatives, until a sequence of incorporated nucleotides is compiled from which the sequence of the template nucleic acid can be determined.

Single molecule sequencing methods of the invention preferably comprise template/primer duplex attached to a surface. Individual nucleotides added to the surface comprise a detectable label—preferably a fluorescent label. Each nucleotide species can comprise a different label, or they can comprise the same label. In a preferred embodiment, each duplex is individually optically resolvable in order to facilitate single molecule sequence discrimination. The choice of a surface for attachment of duplex depends upon the detection method employed. Preferred surfaces for methods of the invention include epoxide surfaces and polyelectrolyte multilayer surfaces, such as those described in Braslavsky, et al., supra. Surfaces preferably are deposited on a substrate that is amenable to optical detection of the surface chemistry, such as glass or silica. The precise surface and substrate used in methods of the invention is immaterial to the functioning of the invention.

The invention provides also compositions for use in a nucleic acid synthesis reaction. In one embodiment, the compositions comprise labeled nucleotide corresponding to a first nucleotide species and at least one nucleotide derivative corresponding to a different nucleotide sequence. Methods and compositions of the invention may take into account that different nucleotides incorporate in an extending primer at different rates and that misincorporation rates similarly vary with the type of nucleotide being incorporated. Accordingly, the identity of the one or more nucleotide derivatives used in methods and compositions of the invention can be varied with the identity of the correct nucleotide sought to be incorporated. For example, if guanidine triphosphate frequently misincorporates at an incorporation site in which adenosine triphosphate should be incorporated, but never misincorporates at an incorporation site in which thymidine triphosphate or cytidine triphosphate should be incorporated, there is no need to add nucleotide derivatives corresponding to thymidine triphosphate or cytidine triphosphate in a synthesis reaction in which guanidine triphosphate is used as the free nucleotide.

According to the invention, a nucleotide derivative forms a hydrogen bond with a complementary nucleotide on a template nucleic acid, but comprises a modification that prohibits the polymerase from incorporating the derivative into the primer because it prevents the formation of a phosphodiester bond with the 3' hydroxyl group of the primer. Preferred nucleotide derivatives comprise a modification to the normal nucleotide triphosphate group to prevent formation of a phosphodiester bond. Preferably, the oxygen bridging the α- and β-phosphates is replaced with another molecule that prevents formation of the phosphodiester bond. Particularly preferred derivatives comprise a substitution of the oxygen molecule bridging the α- and β-phosphate with a carbon, nitrogen or sulfur molecule or a methylene group. Other nucleotide derivatives useful in the invention comprise a modification of the α-, β- or γ-phosphate group. The modification may comprise, for example, the substitution of a bridging or non-bridging oxygen molecule with a thiol, alkyl, carbonyl, amine, alcohol, aryl or an animo acid group.

Nucleotides useful in the invention include any nucleotide or nucleotide analog, whether naturally-occurring or synthetic. For example, preferred nucleotides include phosphate esters of deoxyadenosine, deoxycytidine, deoxyguanosine, deoxythymidine, adenosine, cytidine, guanosine, and uridine.

Polymerases useful in the invention include any nucleic acid polymerase capable of catalyzing a template-dependent addition of a nucleotide or nucleotide analog to a primer. Depending on the characteristics of the target nucleic acid, a DNA polymerase, an RNA polymerase, a reverse transcriptase, or a mutant or altered form of any of the foregoing can be used. According to one aspect of the invention, a thermophilic polymerase is used, such as ThermoSequenase®, 9°N™, Therminator™, Taq, Tne, Tma, Pfu, Tfl, Tth, Tli, Stoffel fragment, Vent™ and Deep Vent™ DNA polymerase.

DETAILED DESCRIPTION

The invention provides methods and compositions for improving the fidelity of a nucleic acid sequencing-by-synthesis reaction by reducing misincorporation of nucleotides. While applicable to bulk sequencing methods, the invention is particularly useful in connection with single molecule sequencing methods. Methods of the invention improve the fidelity of DNA synthesis by blocking misincorporation of a nucleotide triphosphate in template/primer duplexes. According to the invention, when DNA synthesis reaction is performed in the presence of a nucleotide derivative that is complementary to the template nucleotide, the nucleotide derivative forms hydrogen bonds with the template nucleotide, but does not form a phosphodiester bond with the 3' hydroxyl group of the primer. Without incorporating into the primer, the nucleotide derivative is transiently held in place by the hydrogen bonds and blocks the misincorporation of the nucleotide triphosphate.

Figure 2:
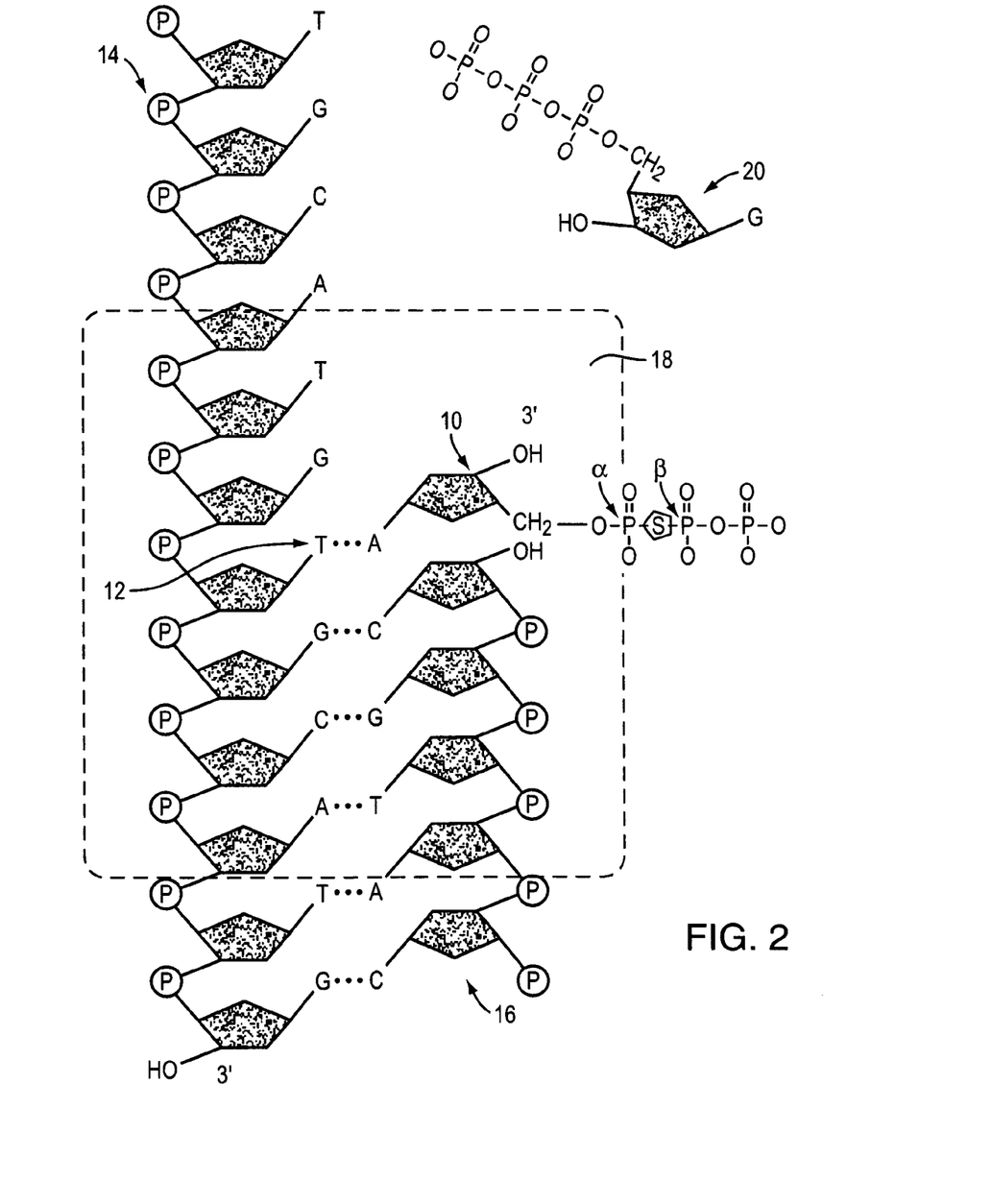
FIG. 2 is a schematic representation of a DNA synthesis reaction performed in the presence of a nucleotide derivative.

FIG. 2 is a schematic representation of DNA synthesis reaction in which a nucleotide derivative (as shown α,β-S-2'-deoxyadenosine 5'-triphosphate) (10) has formed hydrogen bonds with its complementary base (12) located on the template (14) opposite the incorporation site immediately adjacent the 3' terminus of the primer (16). Because the nucleotide derivative lacks an oxygen molecule bridging the α and β phosphate groups, the polymerase (18) is not able to catalyze the formation of a phosphodiester bond between the nucleotide derivative (10) and the 3' hydroxyl group of the primer (16), but because the derivative (10) is blocking the incorporation site at the 3' terminus of the primer (16), the polymerase (18) can not misincorporate an incorrect (i.e., non-complementary) nucleotide (20).

According to the invention, a polymerization reaction is conducted in the presence of a polymerase, at least one labeled dNTP corresponding to a first nucleotide species, and at least one nucleotide derivative corresponding to a different nucleotide species. The nucleotide derivative comprises a modification that inhibits the formation of a phosphodiester bond between the derivative and the 3' hydroxyl group of a primer on a primer/template duplex. If the template comprises a nucleotide opposite the incorporation site that is not complementary to the dNTP, but is complementary to the nucleotide derivative, the polymerase recognizes the nucleotide derivative as complementary to the template nucleotide and brings the derivative into close proximity with the template nucleotide, which facilitates the formation of hydrogen bonds between the derivative and its complementary nucleotide. With the nucleotide derivative blocking the incorporation site, misincorporation of the dNTP is prevented.

Methods and compositions of the invention are particularly well-suited for use in single molecule sequencing techniques. Substrate-bound primer/template duplexes are exposed to a polymerase, a labeled nucleotide corresponding to a first nucleotide species, and at least one nucleotide derivative corresponding to a different nucleotide species. The duplex may be simultaneously exposed to the polymerase, the labeled nucleotide, and the nucleotide derivative; or it may be first exposed to the nucleotide derivative and then to the polymerase and labeled nucleotide. Typically, however, the duplex is simultaneously exposed to the polymerase, the labeled nucleotide, and three nucleotide derivatives, one corresponding to each of the three remaining nucleotide species. The duplexes are washed of unincorporated labeled nucleotides and nucleotide derivatives, and the incorporation of labeled nucleotide is determined. The identity of the nucleotide positioned on the template opposite the incorporate nucleotide is likewise determined. The polymerization reaction is serially repeated in the presence of a labeled nucleotide that corresponds to each of the other nucleotide species in order to compile a sequence of incorporated nucleotides that is representative of the complement to the template nucleic acid.

Certain non-limiting aspects of the invention are further described below in terms of general considerations and examples.

I. General Considerations

A. Nucleotides

Nucleotides useful in the invention as free, unbound nucleotides for incorporation into a primer/template duplex include any nucleotide or nucleotide analog, whether naturally-occurring or synthetic. For example, preferred nucleotides include phosphate esters of deoxyadenosine, deoxycytidine, deoxyguanosine, deoxythymidine, adenosine, cytidine, guanosine, and uridine. Other nucleotides useful in the invention comprise an adenine, cytosine, guanine, thymine base, an xanthine or hypoxanthine; 5-bromouracil, 2-aminopurine, deoxyinosine, or methylated cytosine, such as 5-methylcytosine, and N4-methoxydeoxycytosine. Also included are bases of polynucleotide mimetics, such as methylated nucleic acids, e.g., 2'-O-methRNA, peptide nucleic acids, modified peptide nucleic acids, locked nucleic acids and any other structural moiety that can act substantially like a nucleotide or base, for example, by exhibiting base-complementarity with one or more bases that occur in DNA or RNA and/or being capable of base-complementary incorporation, and includes chain-terminating analogs. A nucleotide corresponds to a specific nucleotide species if they share base-complementarity with respect to at least one base.

Nucleotides for nucleic acid sequencing according to the invention preferably comprise a detectable label. Labeled nucleotides include any nucleotide that has been modified to include a label that is directly or indirectly detectable. Preferred labels include optically-detectable labels, including fluorescent labels or fluorophores, such as fluorescein, rhodamine, derivatized rhodamine dyes, such as TAMRA, phosphor, polymethadine dye, fluorescent phosphoramidite, Texas Red, green fluorescent protein, acridine, cyanine, cyanine 5 dye, cyanine 3 dye, 5-(2'-aminoethyl)-aminonaphthalene-1-sulfonic acid (EDANS), BODIPY, 120 ALEXA or a derivative or modification of any of the foregoing, and also include such labeling systems as hapten labeling. Accordingly, methods of the invention further provide for exposing the primer/target nucleic acid duplex to a digoxigenin, a fluorescein, an alkaline phosphatase or a peroxidase.

B. Nucleotide Derivatives

Nucleotide derivatives useful in the invention include any nucleotide, including those described above in Section A, that forms hydrogen bonds with a complementary nucleotide on a template nucleic acid, but comprises a modification that prevents the formation of a phosphodiester bond with the 3' hydroxyl group of the primer. Preferred nucleotide derivatives will be recognized by the catalytic domain of the polymerase and brought in close proximity with its complementary nucleotide where hydrogen bonding can occur. Accordingly, particularly useful nucleotide derivatives most closely resemble naturally-occurring substrates for polymerases in both chemical formula and structure. Thus, particularly useful nucleotide derivatives comprise phosphate esters of deoxyadenosine, deoxycytidine, deoxyguanosine, deoxythymidine, adenosine, cytidine, guanosine, and uridine. In a preferred embodiment, nucleotide derivatives comprise a triphosphate ester, such as dATP, dCTP, dGTP, dTTP or dUTP. A nucleotide derivative corresponds to a specific nucleotide species if they exhibit the same base-complementarity with respect to at least one base.

According to one feature, a nucleotide derivative comprises a modification of the oxygen bridging the α-phosphate and the β-phosphate in a standard nucleotide triphosphate. For example, preferred modifications include the substitution of the oxygen molecule bridging the α- and β-phosphate groups with a carbon, nitrogen or sulfur molecule or a methylene group. Other nucleotide derivatives useful in the invention comprise a modification of the α-, β- or γ-phosphate group, such as, for example, the substitution of a bridging or non-bridging oxygen molecule with a thiol, alkyl, carbonyl, amine, alcohol, aryl or an animo acid group; or a bulky group that physically interferes with polymerase function. Custom modified nucleotides are commercially available from, for example, TriLink BioTechnologies, Inc., San Diego, Calif., Alexis Biochemicals, Inc., Carlsbad, Calif. and BIOLOG Life Science Institute, Germany.

C. Nucleic Acid Polymerases

Nucleic acid polymerases generally useful in the invention include DNA polymerases, RNA polymerases, reverse transcriptases, and mutant or altered forms of any of the foregoing. DNA polymerases and their properties are described in detail in, among other places, DNA Replication 2nd edition, Kornberg and Baker, W. H. Freeman, New York, N.Y. (1991). Known conventional DNA polymerases useful in the invention include, but are not limited to, Pyrococcus furiosus (Pfu) DNA polymerase (Lundberg et al., 1991, Gene, 108: 1, Stratagene), Pyrococcus woesei (Pwo) DNA polymerase (Hinnisdaels et al., 1996, Biotechniques, 20:186-8, Boehringer Mannheim), Thermus thermophilus (Tth) DNA polymerase (Myers and Gelfand 1991, Biochemistry 30:7661), Bacillus stearothermophilus DNA polymerase (Stenesh and McGowan, 1977, Biochim Biophys Acta 475:32), Thermococcus litoralis (Tli) DNA polymerase (also referred to as Vent™ DNA polymerase, Cariello et al., 1991, Polynucleotides Res, 19: 4193, New England Biolabs), 9°Nm™ DNA polymerase (New England Biolabs), Stoffel fragment, ThermoSequenase® (Amersham Pharmacia Biotech UK), Therminator™ (New England Biolabs), Thermotoga maritima (Tma) DNA polymerase (Diaz and Sabino, 1998 Braz J Med. Res, 31:1239), Thermus aquaticus (Taq) DNA polymerase (Chien et al., 1976, J. Bacteoriol, 127: 1550), DNA polymerase, Pyrococcus kodakaraensis KOD DNA polymerase (Takagi et al., 1997, Appl. Environ. Microbiol. 63:4504), JDF-3 DNA polymerase (from thermococcus sp. JDF-3, Patent application WO 0132887), Pyrococcus GB-D (PGB-D) DNA polymerase (also referred as Deep Vent™ DNA polymerase, Juncosa-Ginesta et al., 1994, Biotechniques, 16:820, New England Biolabs), UlTma DNA polymerase (from thermophile Thermotoga maritima; Diaz and Sabino, 1998 Braz J. Med. Res, 31:1239; PE Applied Biosystems), Tgo DNA polymerase (from thermococcus gorgonarius, Roche Molecular Biochemicals), *E. coli* DNA polymerase I (Lecomte and Doubleday, 1983, Polynucleotides Res. 11:7505), T7 DNA polymerase (Nordstrom et al., 1981, J Biol. Chem. 256:3112), and archaeal DP1I/DP2 DNA polymerase II (Cann et al., 1998, Proc Natl Acad. Sci. USA 95:14250-->5).

While mesophilic polymerases are contemplated by the invention, preferred polymerases are thermophilic. Thermophilic DNA polymerases include, but are not limited to, ThermoSequenase®, 9°Nm™, Therminator™, Taq, Tne, Tma, Pfu, Tfl, Tth, Tli, Stoffel fragment, Vent™ and Deep Vent™ DNA polymerase, KOD DNA polymerase, Tgo, JDF-3, and mutants, variants and derivatives thereof.

Reverse transcriptases useful in the invention include, but are not limited to, reverse transcriptases from HIV, HTLV-1, HTLV-II, FeLV, FIV, SIV, AMV, MMTV, MoMuLV and other retroviruses (see Levin, Cell 88:5-8 (1997); Verma, Biochim Biophys Acta. 473:1-38 (1977); Wu et al., CRC Crit Rev Biochem. 3:289-347 (1975)).

Certain embodiments of the invention are described in the following examples, which are not meant to be limiting.

EXAMPLE 1

Single Molecule Sequencing Using Nucleotide Derivatives

The following nucleotide derivatives, each comprising a substitution of the oxygen molecule bridging the α and β phosphate groups with a sulfur molecule, are prepared: α,β-S-2'-deoxyadenosine 5'-triphosphate; α,β-S-2'-deoxycytidine 5'-triphosphate; α,β-S-2'-deoxyguanosine 5'-triphosphate; and α,β-S-2'-deoxythymidine 5'-triphosphate. Primer/template duplexes are bound to a solid support in a concentration that results in individually optically resolvable duplexes. The bound duplexes are subjected to serial sequencing-by-synthesis cycles in which a polymerase, labeled standard nucleotide, and nucleotide derivatives corresponding to each of the three non-standard nucleotide species are combined. The incorporation of a labeled nucleotide is determined, recorded and the reaction serially repeated with labeled nucleotide corresponding to each of the different nucleotide species and the appropriate nucleotide derivatives in order to compile a sequence that is representative of the complement of the target nucleic acid.

EXAMPLE 2

Assay for the Inhibition of Polymerase Activity

A simple assay may be performed to assess the ability of a usefulness of nucleotide derivative in methods and compositions of the invention.

Primed DNA template is diluted into an appropriate volume of 20 mM Tris-HCl, pH 7.5 and the enzyme is diluted into an appropriate volume of 20 mM Tris-HCl, containing 2 mM β-mercaptoethanol, and 100 mM KCl. 0.05 mg/mL primed DNA template and 0.01 U/μL DNA polymerase are pipetted into microcentrifuge tubes or a 96-well plate in a 50 μL reaction volume. 1.6 μM nucleotide derivative is added to the test reactions. Blank reactions excluding enzyme and control reactions excluding test compound are also prepared using enzyme dilution buffer and test compound solvent, respectively. The reaction is initiated with reaction buffer with the following components 20 mM Tris-HCl, pH 7.5; 200 μg/mL bovine serum albumin; 100 mM KCl; 2 mM β-mercaptoethanol; 10 mM MgCl$_2$, 1.6 μM dATP, dGTP, dCTP, and dTTP; and α-$^{33}$P-dAT. The reaction is incubated for sixty minutes at 37° C. and then quenched by the addition of 20 μL of 0.5M EDTA. 50 μL of the quenched reaction is spotted onto Whatman DE81 filter disks and air dried. The filter disks are repeatedly washed with 150 mL 0.3M ammonium formate, pH 8 until 1 mL of wash is <100 cpm. The disks are washed twice with 150 mL absolute ethanol and once with 150 mL anhydrous ether, dried and counted in 5 mL scintillation fluid.

The percentage of inhibition of the test is calculated according to the following equation: % inhibition={1−(cpm in test reaction−cpm in blank)/(cpm in control reaction−cpm in blank)}×100.

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes which come within the meaning and range of equivalency of the claims are therefore intended to be embraced therein

I claim:

1. A method for inhibiting nucleotide misincorporation in a nucleic acid synthesis reaction, the method comprising conducting a polymerization reaction on a nucleic acid duplex comprising a template and a primer in the presence of
    a nucleic acid polymerase, a first detectably labeled nucleotide corresponding to a first nucleotide species complementary to the position opposite the incorporation site at the 3' terminus of the primer,
    a second nucleotide of a different species, and
    at least one nucleotide derivative, each of the nucleotide derivatives corresponding to a different nucleotide species than the first nucleotide species,
        wherein each nucleotide derivative comprises a modification that inhibits formation of a phosphodiester bond between the nucleotide derivative and a free 3' hydroxyl on a primer nucleotide.

2. The method of claim 1 further comprising removing nucleotide derivatives and nucleotides that are not incorporated into the primer.

3. The method of claim 2 further comprising the step of repeating said conducting and removing steps using a second nucleotide species and a nucleotide derivative corresponding to a nucleotide species different from said second species.

4. The method of claim 1 wherein said nucleotide derivative comprises a triphosphate group lacking an oxygen between an α-phosphate and a β-phosphate such that said nucleotide derivative is prevented from forming a phosphodiester bond with said free 3' hydroxyl group on the primer.

5. The method of claim 4 wherein said derivative comprises substitution of an oxygen molecule with a carbon, nitrogen or sulfur molecule.

6. The method of claim 4 wherein said derivative comprises substitution of an oxygen molecule with a methylene group.

7. The method of claim 4 wherein said derivative comprises substitution of an oxygen molecule with a thiol, alkyl, carbonyl, amine, alcohol, aryl or an amino acid group.

8. The method of claim 1 wherein, if said template comprises a nucleotide opposite a position immediately adjacent to a 3' terminus of the primer that is complementary to said nucleotide derivative but not complementary to said first nucleotide, said nucleotide derivative forms a hydrogen bond with its complementary nucleotide so as to prevent said first nucleotide from bonding thereto and misincorporating into said primer in said nucleic acid synthesis reaction.

9. The method of claim 1 wherein said nucleic acid duplex is bound to a solid support.

10. The method of claim 1 comprising a plurality of said duplex, each member of said plurality being individually optically resolvable.

11. A method for sequencing a nucleic acid, the method comprising the steps of: (a) exposing a nucleic acid duplex comprising a template and a primer to a nucleic acid polymerase, a first labeled nucleotide, and at least one nucleotide derivative corresponding to a nucleotide species different from said first nucleotide; wherein said nucleotide derivative comprises a modification that inhibits formation of a phosphodiester bond between the nucleotide derivative and a 3' hydroxyl group of the primer, and (b) removing nucleotide derivatives and labeled nucleotides that are not incorporated into the primer; (c) determining incorporation of the labeled nucleotide and thereby identifying a nucleotide that is complementary to a nucleotide at a position on said template opposite the incorporated labeled nucleotide; and (d) repeating steps (a), (b) and (c) with a second labeled nucleotide and at least one nucleotide derivative corresponding to a nucleotide species different from said second labeled nucleotide.

12. The method of claim 11 wherein said nucleotide derivative comprises a triphosphate group having a molecule other than oxygen between an α-phosphate and β-phosphate.

13. The method of claim 12 wherein said derivative comprises substitution of an oxygen molecule with a carbon, nitrogen or sulfur molecule.

14. The method of claim 12 wherein said derivative comprises a substitution of an oxygen molecule with a methylene group.

15. The method of claim 2 wherein said nucleotide derivative comprises a triphosphate group having a modified α- or β-phosphate.

16. The method of claim 15 wherein said modification comprises a substitution of an oxygen molecule with a thiol, alkyl, carbonyl, amine, alcohol, aryl or an amino acid group.

17. The method of claim 11 wherein said exposing step is performed in the presence of at least two nucleotide derivatives, each derivative corresponding to a nucleotide species different from said first nucleotide.

18. The method of claim 11 wherein said exposing step is performed in the presence of three nucleotide derivatives, each derivative corresponding to a nucleotide species different from said first nucleotide.

19. The method of claim 11 further comprising the step of compiling a sequence of nucleotides incorporated into said primer.

20. The method of claim 11 wherein said labeled nucleotide comprises a labeled dNTP.

21. The method of claim 11 wherein said first nucleotide is a deoxyadenosine triphosphate and said at least one nucleotide derivative corresponds to a nucleotide species selected from the group consisting of deoxyguanosine triphosphate, deoxycytidine triphosphate, and deoxyuridine triphosphate.

22. The method of claim 11 wherein said first nucleotide is a deoxyguanosine triphosphate thereof and said at least one nucleotide derivative corresponds to a nucleotide species selected from the group consisting of deoxyadenosine triphosphate, deoxycytidine triphosphate and deoxyuridine triphosphate.

23. The method of claim 11 wherein said first nucleotide is a deoxycytidine triphosphate thereof and said three nucleotide derivatives corresponds to the nucleotide species of deoxyadenosine triphosphate, deoxyguanosine triphosphate and deoxyuridine triphosphate.

24. The method of claim 11 wherein said first nucleotides is a deoxyuridine triphosphate thereof and said at least one nucleotide derivative corresponds to a nucleotide species selected from the group consisting of deoxyadenosine triphosphate, deoxyguanosine triphosphate and deoxycytidine triphosphate.

25. The method of claim 18 wherein said first nucleotide is a deoxyadenosine triphosphate thereof and said three nucleotide derivatives correspond to deoxyguanosine triphosphate, deoxycytidine triphosphate, and deoxyuridine triphosphate.

26. The method of claim 18 wherein said first nucleotide is a deoxyguanosine triphosphate and said three nucleotide derivatives correspond to deoxyadenosine triphosphate, deoxycytidine triphosphate and deoxyuridine triphosphate.

27. The method of claim 18 wherein said first nucleotide is a deoxycytidine triphosphate and said three nucleotide derivatives correspond to deoxyadenosine triphosphate, deoxyguanosine triphosphate and deoxyuridine triphosphate.

28. The method of claim 18 wherein said first nucleotide is a deoxyuridine triphosphate and said three nucleotide derivatives correspond to deoxyadenosine triphosphate, deoxyguanosine triphosphate and deoxycytidine triphosphate.

29. The method of claim 11, wherein said exposing step comprises first exposing said nucleic acid duplex to said at least one nucleotide derivative, then exposing said nucleic acid duplex to said nucleic acid polymerase and said labeled nucleotide.

30. The method of claim 1 wherein the polymerization reaction is conducted in the presence of three different species of nucleotide derivatives.

* * * * *